(12) United States Patent
Srinivasan et al.

(10) Patent No.: US 9,920,058 B2
(45) Date of Patent: Mar. 20, 2018

(54) MOLECULES WITH POTENT DHFR BINDING AFFINITY AND ANTIBACTERIAL ACTIVITY

(71) Applicant: Georgia Tech Research Corporation, Atlanta, GA (US)

(72) Inventors: Bharath Srinivasan, Atlanta, GA (US); Jeffrey Skolnick, Atlanta, GA (US); Hongyi Zhou, Marietta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 14/269,495

(22) Filed: May 5, 2014

(65) Prior Publication Data
US 2014/0329840 A1 Nov. 6, 2014

Related U.S. Application Data

(60) Provisional application No. 61/819,956, filed on May 6, 2013.

(51) Int. Cl.
*C07D 487/04* (2006.01)
*A01N 43/90* (2006.01)

(52) U.S. Cl.
CPC .................... *C07D 487/04* (2013.01)

(58) Field of Classification Search
None
See application file for complete search history.

(56) References Cited

U.S. PATENT DOCUMENTS

| | | | |
|---|---|---|---|
| 4,118,561 A * | 10/1978 | Ledig | 544/250 |
| 4,889,645 A | 12/1989 | Firth, Jr. | |
| 5,891,922 A | 4/1999 | Gaumer | |
| 7,253,177 B2 | 8/2007 | Lin | |
| 8,097,265 B2 | 1/2012 | Biering | |
| 8,563,017 B2 | 10/2013 | Cunningham | |
| 2001/0053333 A1 | 12/2001 | Messier | |

OTHER PUBLICATIONS

Adane et al. in Chem. Biol. Drug Disc. 2010:75: 115-126.*
Llarrull et al. in Antimicrobial Agents and Chemotherapy 53(10), 40151-4063 (2009).*
Methicillin structure in www.chemicalbook.com/ProdSupplierGNCB3889080_EN.htm. (retrieved from the internet Jan. 18, 2016).*
Sader et al. in Antimicrobial Agents and Chemotherapy 53(5), 2171-2175 (2009).*
Microbiology Online at www.microbiologyonline. org.uk/about-microbiology/microbes-and-the-human-body/microbes-and-disease (retrieved from the internet Jan. 19, 2016).*
Frey et al. in Journal of Molecular Biology 387, 1298-1308 (2009).*
Floris et al. in Curr Med Res Opin 26(7):1565-78 (2010) (Year: 2010).*
Adane, et al., "Shape- and chemical feature-based 3D-pharmacophore model generation and virtual screening: identification of potential leads for P. falciparum DHFR enzyme inhibition", Chem Biol Drug Des., 75:115-26 (2010).
Alonso, et al., "Protein tyrosine phosphatases in the human genome", Cell, 117(6):699-711 (2004).
Babaoglu, et al., "Comprehensive mechanistic analysis of hits from high-throughput and docking screens against beta-lactamase", J. Med. Chem.,, 51(8):2502-11 (2008).
Bajorath , et al., "Integration of virtual and high-throughput screening", Nat Rev Drug Discov., 1(11):882-94 (2002).
Boucher, et al., "Structural and biochemical characterization of a mitochondrial peroxiredoxin from Plasmodium falciparum", Mol. Microbiol., 61(4):948-59 (2006).
Bowers, et al., "Virtual ligand screening of the p300/CBP histone acetyltransferase: identification of a selective small molecule inhibitor", Chem Biol., 17(5):471-82 (2010).
Brylinski, et al., "FINDSITE: a threading-based approach to ligand homology modeling", PLoS Computational Biology , 5(6):e1000405 (2009).
Brylinski, et al., "A threading-based method (FINDSITE) for ligand-binding site prediction and functional annotation", PNAS, 105:129-34 (2008).
Chen, et al., "Thymidylate synthase and dihydrofolate reductase expression in non-small cell lung carcinoma: the association with treatment efficacy of pemetrexed", Lung Cancer, 74(1):132-8 (2011).
Chio, et al., "Identification of highly potent and selective inhibitors of Toxoplasma gondii dihydrofolate reductase", Antimicrob Agents Chemother.m 37(9):1914-23 (1993).
Cross, et al., "Comparison of several molecular docking programs: pose prediction and virtual screening accuracy", J. Chem Info. Model., 49:1455-74 (2009).
Crowther, et al., "Use of thermal melt curves to assess the quality of enzyme preparations1", AnalvbTab Biochem., 399(2):268-75 (2010).
Doman, et al., "Molecular docking and high-throughput screening for novel inhibitors of protein tyrosine phosphatase-1B", J Med Chem., 45(11):2213-21 (2002).
Drews , "Drug discovery: a historical perspective", Science, 287(5460):1960-4 (2000).
Gaulton, et al., "ChEMBL: a large-scale bioactivity database for drug discovery", Nucl Acid Res, 40(D1):D1100-7 (2012).
Gozalbes, et al., "Development and experimental validation of a docking strategy for the generation of kinase-targeted libraries", J Med Chem., 51(11):3124-32 (2008).
Gruneberg, et al., "Successful virtual screening for novel inhibitors of human carbonic anhydrase: strategy and experimental confirmation", J. Med Chem., 45(17):3588-3602 (2002).
Ham, et al., "Mechanism of Cell Growth Inhibition by Menadione", B Kor Chem Soc, 23(10):1371-2 (2002).

(Continued)

*Primary Examiner* — Dennis Heyer
(74) *Attorney, Agent, or Firm* — Smith, Gambrell & Russell, LLP

(57) ABSTRACT

7-(substituted) derivatives of 7H-pyrrolo[3,2-f]-quinazoline-1,3-diamines, derivative thereof, and methods of using them are provided. The pharmaceutical formulations prepared from the compounds can be used to treat a variety of conditions, which include, but are not limited to bacterial and fungal infections. The compounds can also be used as a sterilizing or disinfecting agent.

9 Claims, 4 Drawing Sheets

(56) References Cited

OTHER PUBLICATIONS

Henikoff, et al., "Amino acid substitution matrices from protein blocks", PNAS, 89:10915-9 (1992).
Hert, et al., "New methods for ligand-based virtual screening: use of data fusion and machine learning to enhance the effectiveness of similarity searching", J. Chem. Info.Model., 46(2):462-70 (2006).
Huang, et al., "Benchmarking sets for molecular docking", J. Med. Chem., 49(23):6789-801 (2006).
Irwin, et al., "ZINC—a free database of commercially available compounds for virtual screening", J Chem Inf Model, 45:177-82 (2005).
Klebe, "Virtual ligand screening: strategies, perspectives and limitations", Drug Discov Today, 11(13-14):580-94 (2006).
Kroemer, et al., "Structure-based drug design: docking and scoring", Curr Protein Pept Sci., 8(4):312-28 (2007).
Kuyper, et al., "High-affinity inhibitors of dihydrofolate reductase: antimicrobial and anticancer activities of 7,8-dialkyl-1,3-diaminopyrrolo[3,2-f]quinazolines with small molecular size", J. Med. Chem., 39(4):892-903 (1996).
Liu, et al., "Clinical practice guidelines by the infectious diseases society of america for the treatment of methicillin-resistant *Staphylococcus aureus* infections in adults and children", Clin Infect Dis., 52(3):e18-55 (2011).
Lo, et al., "Evaluation of fluorescence-based thermal shift assays for hit identification in drug discovery", Anal Biochem., 332(1):153-9 (2004).
Lynch, et al., "Emergence of a dhfr mutation conferring high-level drug resistance in Plasmodium falciparum populations from southwest Uganda", J. Infect. Dis., 197(11):1598-604 (2008).
McCutchan, et al., "Use of malaria rapid diagnostic test to identify Plasmodium knowlesi infection", Emerg. Infect. Dis., 14(11):1750-2 (2008).
Molina, "Pralatrexate, a dihydrofolate reductase inhibitor for the potential treatment of several malignancies", IDrugs, 11(7):508-21 (2008).
Navadgi, et al., "The two Plasmodium falciparum nucleosome assembly proteins play distinct roles in histone transport and chromatin assembly", J. Biol Chem., 281(25):16978-84 (2006).
Niesen, et al., "The use of differential scanning fluorimetry to detect ligand interactions that promote protein stability", Nature Protocols, 2(9):2212-21 (2007).
Pandit, et al., "Fr-TM-align: a new protein structural alignment method based on fragment alignments and the TM-score", BMC Bioinformatics,(9):531 (2008).
Park, et al., "Aminoacyl tRNA synthetases and their connections to disease", PNAS., 105(32):11043-9 (2008).
Polgar, et al., "Comparative virtual and experimental high-throughput screening for glycogen synthase kinase-3beta inhibitors", J. Med Chem, 48(25):7946-59 (2005).
Ponts, et al., "Deciphering the ubiquitin-mediated pathway in apicomplexan parasites: a potential strategy to interfere with parasite virulence", PloS One, 3(6):e2386 (2008).
Reddy, et al., "Virtual screening in drug discovery—a computational perspective", Curr Protein Pept Sci., 8(4):329-51 (2007).
Rice, "Emergence of vancomycin-resistant enterococci", Emerg Infect Dis., 7(2):183-7 (2001).
Richardson, et al., "Structural studies on bioactive compounds. 39. Biological consequences of the structural modification of DHFR-inhibitory 2,4-diamino-6-(4-substituted benzylamino-3-nitrophenyl)-6-ethylpyrimidines (benzoprims)", J. Med. Chem., 47(16):4105-13 (2004).
Schimke, et al., "Gene amplification and drug resistance in cultured murine cells", Science, 202(4372):1051-5 (1978).
Schnell, et al., "Structure, dynamics, and catalytic function of dihydrofolate reductase", Annual Rev Biophys Biomel Struc., 33:119-40 (2004).
Srinivasan, et al., "Experimental validation of FINDSITEcomb virtual ligand screening results for eight proteins yields novel nanomolar and micromolar binders", J Cheminfo., 6:16 (2014).
Taylor, et al., "Signaling through cAMP and cAMP-dependent protein kinase: diverse strategies for drug design", Biochimica Biophysica Acta, 1784(1):16-26 (2008).
Teasdale, et al., "Bromophycoic acids: bioactive natural products from a Fijian red alga *Callophycus* sp", J Organic Chem., 77(18):8000-6 (2012).
Terstappen, et al., "Target deconvolution strategies in drug discovery", Nat Rev Drug Discov., 6(11):891-3 (2007).
Trott and Olson, et al., "AutoDock Vina: improving the speedand accuracy of docking with a new scoring function,efficient optimization, and multithreading", J. Comp., Chem., 31:455-61 (2010).
Wang, et al., "PubChem's BioAssay Database", Nucleic Acids Res., 40(Database issue):D400-412 (2012).
Wass, et al., "3DLigandSite: predicting ligand-binding sites using similar structures", Nucleic Acids Res., 38(Web Server issue):W469-473 (2010).
Willems, et al., "Global spread of vancomycin-resistant Enterococcus faecium from distinct nosocomial genetic complex", Emerg Infect Dis., 11(6):821-8 (2005).
Wishart, et al., "DrugBank: a comprehensive resource for in silico drug discovery and exploration", Nucl Acid Res, 34(Database):D668-672 (2006).
Wongsrichanalai, et al., "Epidemiology of drug-resistant malaria", Lancet Infect. Dis., 2(4):209-18. (2002).
Zhou, et al., "FINDSITE(X): a structure-based, small molecule virtual screening approach with application to all identified human GPCRs", Mol Pharm., 9(6):1775-84 (2012).
Zhou and Skolnick, et al., "Template-based protein structure modeling using TASSERVMT", Proteins, 80(2):352-61 (2011).
Zhou and Skolick, et al., FINDSITEcomb: A Threading/Structure-Based, Proteomic-Scale Virtual Ligand Screening Approach J. Chem., Info. & Model., 53(1):230-40 (2013).
Zolli-Jjuran, et al., "High throughput screening identifies novel inhibitors of *Escherichia coli* dihydrofolate reductase that are competitive with dihydrofolate.", Bioorganic & Med. Chem. Lett., 13(15):2493-96 (2003).

\* cited by examiner

MOLECULES WITH POTENT DHFR BINDING AFFINITY AND ANTIBACTERIAL ACTIVITY

CROSS-REFERENCE TO RELATED APPLICATIONS

This application claims the benefit of priority to U.S. Ser. No. 61/819,956, filed on May 6, 2013, the disclosure of which incorporated herein by reference.

STATEMENT REGARDING FEDERALLY SPONSORED RESEARCH

This invention was made with government support under Grant RO1 GM037408 and RO1 GM048835 awarded by the National Institutes of Health. The government has certain rights in the invention.

FIELD OF THE INVENTION

The invention is generally directed to methods of treating microbial infections or hyperproliferative conditions.

BACKGROUND OF THE INVENTION

Despite impressive successes in controlling or eliminating bacterial infections by antibiotics, the widespread use of antibiotics both in human medicine and as a feed supplement in poultry and livestock production has led to drug resistance in many pathogenic bacteria. Systematic incorporation of mutations in the protein dihydrofolate reductase (DHFR) is one mechanism microbes acquire resistance to antibiotics. The appearance of antibiotic resistance in many pathogenic bacteria, in many cases involving multi-drug resistance, has raised the specter of a pre-antibiotic era in which many bacterial pathogens are simply untreatable by medical intervention. Various drug resistant bacteria such as methicillin-resistant *Staphylococcus aureus* (MRSA), vancomycin-resistant Enterococci (VRE) and penicillin-resistant *Streptococcus pneumoniae* (PRSP) have been emerging in recent years.

Patients who are infected with such drug resistant bacteria have limited treatment options. Moreover, the emergence of multi-drug resistant bacteria is of serious concern worldwide as they cause intractable infectious diseases.

Thus, there is a need to identify compounds which can act as antibacterials, and more importantly, which can combat the rising incidences of drug-resistant bacterial infections.

It is therefore an object of the present invention to provide compounds with antibacterial activity, which can be used to combat drug resistant bacterial infections.

It is also an object of the present invention to provide compounds with antibacterial activity, which can be used to treat bacterial infections acquired as a result of a hospital stay.

SUMMARY OF THE INVENTION

Nine compounds that inhibit dihydrofolate reductase (DHFR) activity have been identified. These compounds include the compounds having the following NSC numbers: 309401, 80735, 123458, 157522, 159686, 379536, 50690, 55152, and 130801. A preferred DHFR inhibitor is NSC309401 also referred to as 7-(substituted) 7H-pyrrolo [3,2-f]-quinazoline-1,3-diamine and CAS No. 77681-42-6. Derivatives of these DHFR inhibitors and methods of their use are also provided. The compounds can be used to inhibit DHFR in microbes or cancer cells.

One embodiment provides NSC309401, represented by formula I, below.

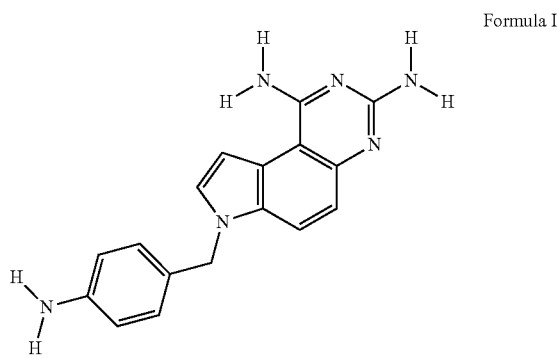 [SMILES: Nc1ccc(Cn2ccc3c4c(N)nc(N)nc4ccc32)cc1]

Formula I or a derivative thereof.

It has been discovered that NSC309401 is an antifolate with potent binding to DHFR. It has also been discovered that NSC309401 has antibacterial activity. In particular, it has been discovered that NSC309401 has antibacterial activity against multi-drug resistant bacteria including, but not limited to, multi-drug resistant *E. coli* (MDREC), methicillin-resistant *Staphylococcus aureus* (MRSA), vancomycin-resistant *Enterococcus faecium* (VREF), *E. coli* strain DH5 alpha, or combinations thereof. It has also been discovered that NSC309401 has antifungal activity against, for example, amphotericin-resistant *Candida albicans* (ARCA)

NSC309401, 80735, 123458, 157522, 159686, 379536, 50690, 55152, and 130801, or derivatives thereof can be administered as the neutral free acid or free base or can be administered as a pharmaceutically acceptable acid-addition or base-addition salt. Additionally, these compounds or derivatives thereof can be formulated with one or more pharmaceutically acceptable excipients to prepare pharmaceutical compositions. The compounds can be administered by a variety of routes of administration including enteral, parenteral, topical, or transmucosal.

The pharmaceutical formulations prepared from the compounds disclosed herein can be used to treat a variety of microbial infections which include, but are not limited to skin infections, eye infections, lung infections, urinary tract infections, or blood infections. The infections can be caused by bacteria including but not limited to methicillin-resistant *Staphylococcus aureus*, *Enterococcus faecalis* and vancomycin-resistant strains of *Enterococcus faecium* (VREF) or by fungi such as *Candida albicans*.

NSC309401, 80735, 123458, 157522, 159686, 379536, 50690, 55152, and 130801 or derivatives thereof can also be used as a sterilizing or disinfecting agent. For example, the compounds can be used to coat or clean surfaces including but not limited to medical surfaces, medical devices, or medical instruments.

DETAILED DESCRIPTION OF THE INVENTION

I. Definitions

Figure 1:
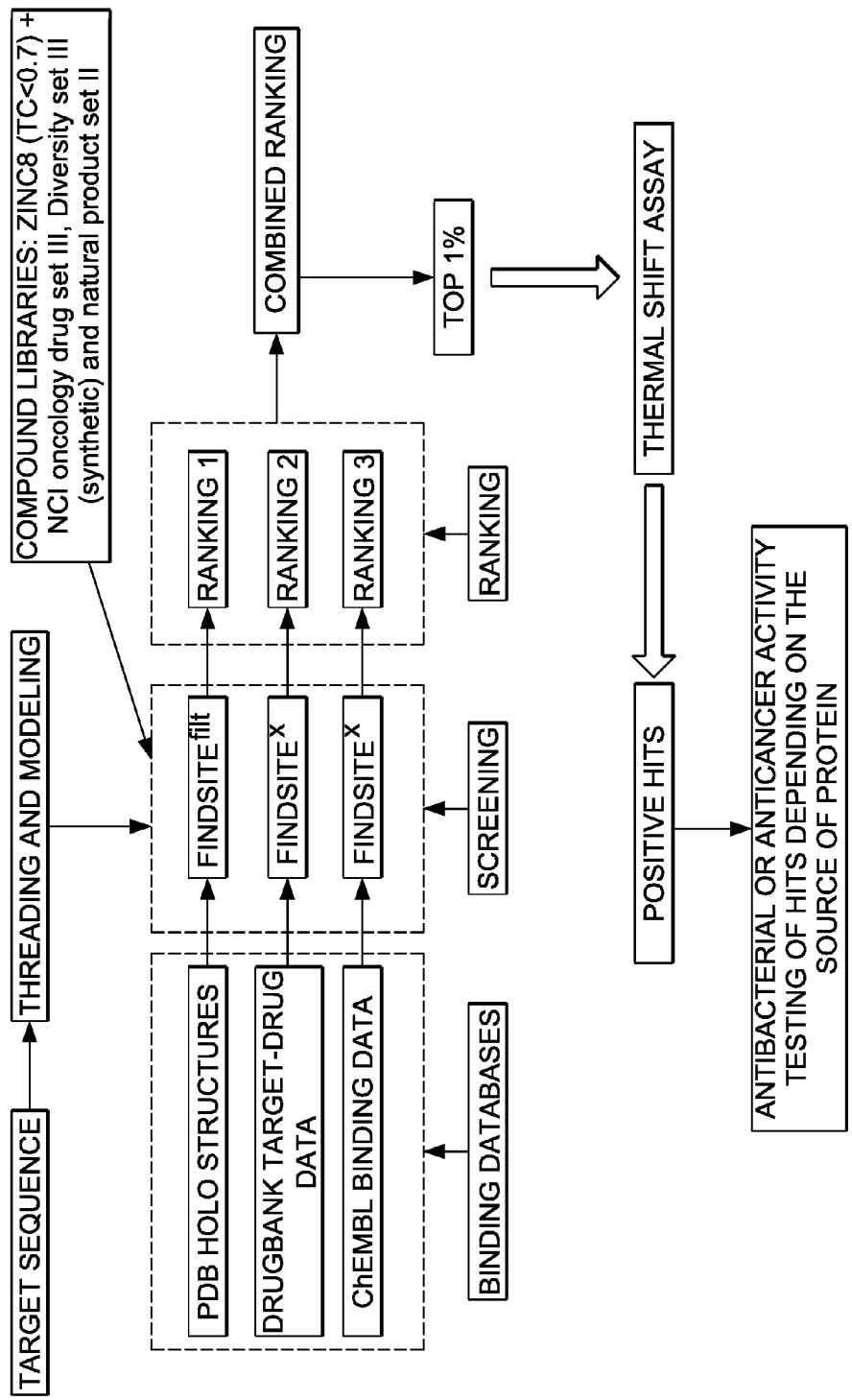
FIG. 1 shows the flowchart of FINDSITE$^{comb}$ methodology (Zhou, et al., *J. Chem., Info. & Model.*, 53(1):230-240 (2013)) in combination with experimental validation protocol.
Figure 2A:
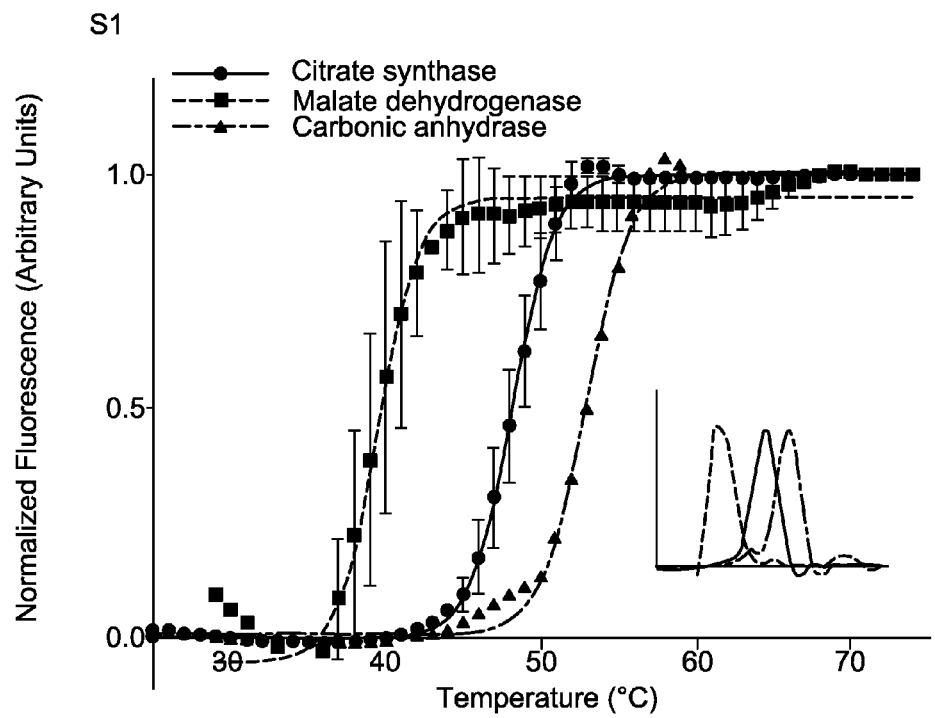
FIGS. 2A-2D shows the thermal shift data for various enzymes (citrate synthase, malate dehydrogenase and carbonic anhydrase (FIG. 2A); Carbonic anhydrase plus or minus various concentrations of TFMSA (FIG. 2B), citrate synthase plus/minus oxaloacetate (FIG. 2C) and malic dehydrogenase plus/minus NADH.
Figure 2B:
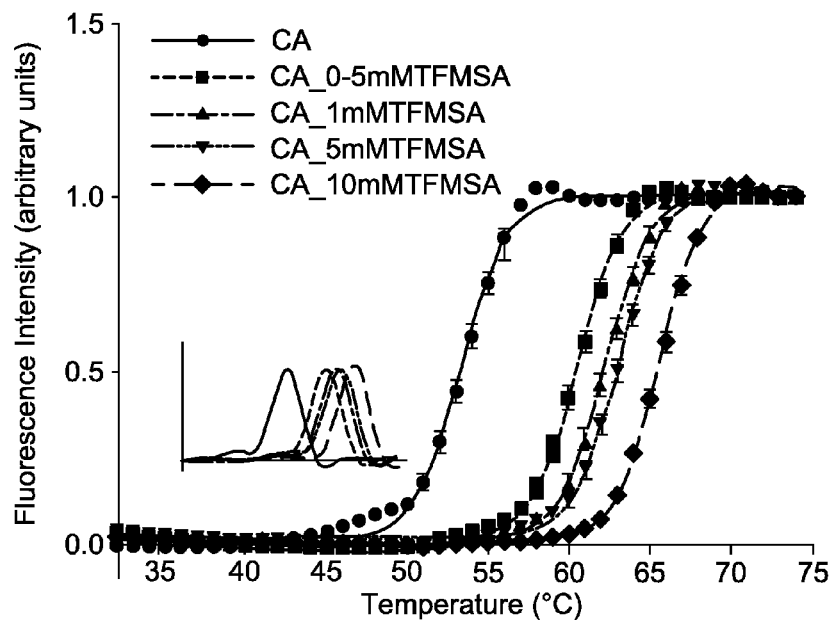
Figure 2C:
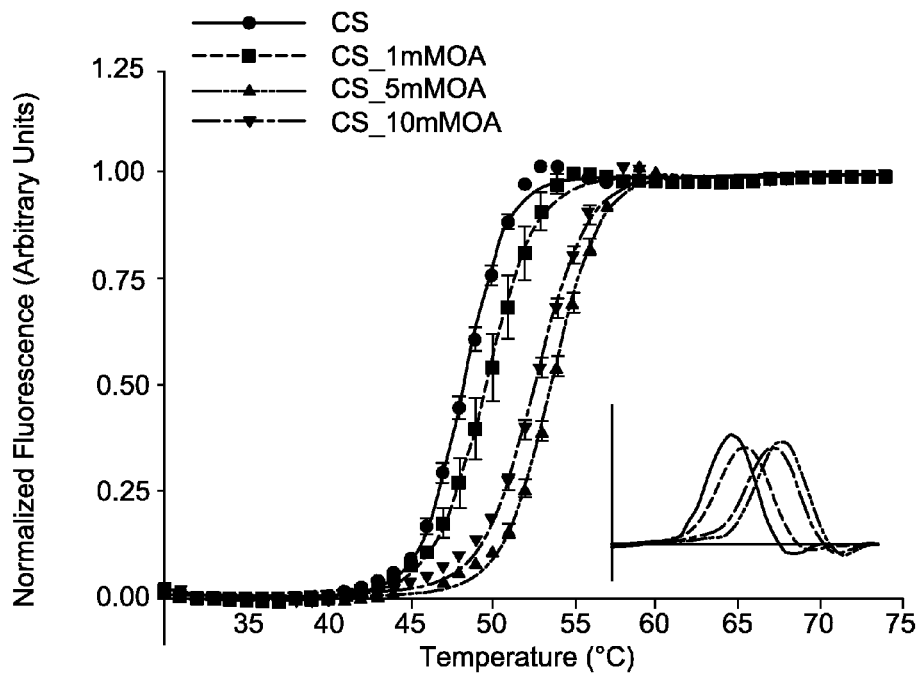
Figure 2D:
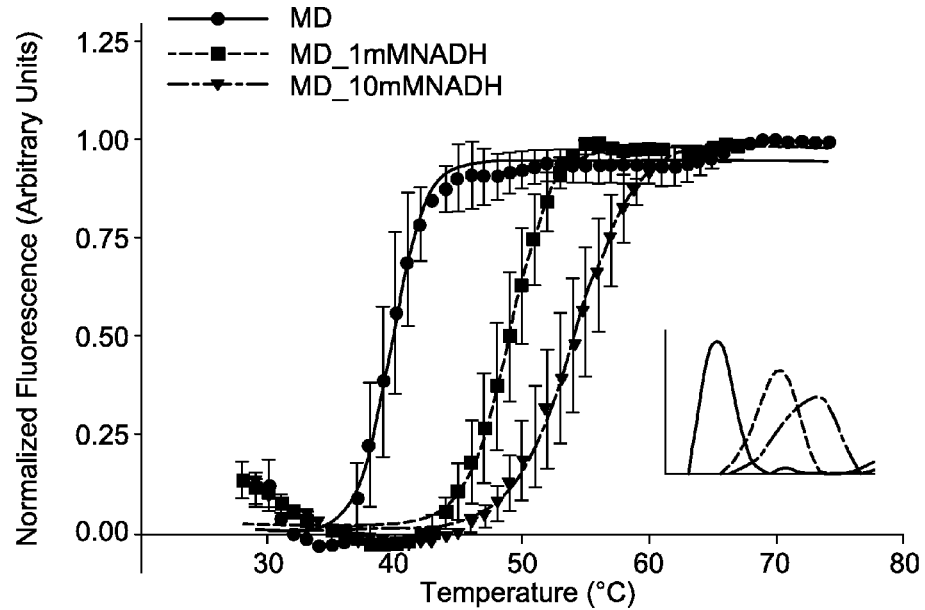

"Aerosol" as used herein refers to any preparation of a fine mist of particles, which can be in solution or a suspension, whether or not it is produced using a propellant.

"Amphiphilic" as used herein refers to a molecule combining hydrophilic and lipophilic (hydrophobic) properties.

A "continuous phase" refers to the liquid in which solids are suspended or droplets of another liquid are dispersed, and is sometimes called the external phase. This also refers to the fluid phase of a colloid within which solid or fluid particles are distributed. If the continuous phase is water (or another hydrophilic solvent), water-soluble or hydrophilic drugs will dissolve in the continuous phase (as opposed to being dispersed). In a multiphase formulation (e.g., an emulsion), the discreet phase is suspended or dispersed in the continuous phase.

A "cream" is a viscous liquid or semi-solid emulsion of either the "oil-in-water" or "water-in-oil type".

An "emulsion" is a composition containing a mixture of non-miscible components homogenously blended together.

"Gel" as used herein is a colloid in which the dispersed phase has combined with the continuous phase to produce a semisolid material, such as jelly.

"Hydrophilic" as used herein refers to substances that have strongly polar groups that readily interact with water.

"Hydrophobic" as used herein refers to substances that lack an affinity for water; tending to repel and not absorb water as well as not dissolve in or mix with water.

"Lipophilic" as used herein refers to compounds having an affinity for lipids.

A "lotion" is a low- to medium-viscosity liquid formulation.

"Oil" as used herein refers to a composition containing at least 95% wt. of a lipophilic substance. Examples of lipophilic substances include but are not limited to naturally occurring and synthetic oils, fats, fatty acids, lecithins, triglycerides and combinations thereof.

An "ointment" is a semisolid preparation containing an ointment base and optionally one or more active agents.

"Parenteral administration", as used herein, means administration by any method other than through the digestive tract or non-invasive topical or regional routes.

"Patient" or "subject" to be treated as used herein refers to either a human or non-human animal.

"Pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

"Pharmaceutically acceptable salt", as used herein, refers to derivatives of the compounds defined herein, wherein the parent compound is modified by making acid or base salts thereof.

"Therapeutically effective" or "effective amount" as used herein means that the amount of the composition used is of sufficient quantity to ameliorate one or more causes or symptoms of a disease or disorder. Such amelioration only requires a reduction or alteration, not necessarily elimination. As used herein, the terms "therapeutically effective amount" "therapeutic amount" and "pharmaceutically effective amount" are synonymous. One of skill in the art can readily determine the proper therapeutic amount.

A "subject" or "patient" refers to a human, primate, non-human primate, laboratory animal, farm animal, livestock, or a domestic pet.

"Cleaning formulation", as used herein, means a composition suitable for application to a surface for removing dirt, oils, and the like, for disinfecting, or a combination thereof. Cleaning compositions can be antibacterial, antimicrobial, or both. Cleaning compositions can be suitable for use on the human skin meaning that all components of the composition are present at concentrations that cause no significant signs of irritation when applied to human skin. As used herein, "significant signs of irritation" include erythema, redness, and/or swelling at the site of injection at the site of application, necrosis at the site of application, exfoliative dermatitis at the site of application, and severe pain that prevents daily activity and/or requires medical attention or hospitalization.

The term "alkyl" refers to the radical of saturated aliphatic groups (i.e., an alkane with one hydrogen atom removed), including straight-chain alkyl groups, branched-chain alkyl groups, cycloalkyl(alicyclic) groups, alkyl-substituted cycloalkyl groups, and cycloalkyl-substituted alkyl groups.

In preferred embodiments, a straight chain or branched chain alkyl has 30 or fewer carbon atoms in its backbone (e.g., C1-C30 for straight chains, and C3-C30 for branched chains), preferably 20 or fewer, more preferably 15 or fewer, most preferably 10 or fewer. Likewise, preferred cycloalkyls have 3-10 carbon atoms in their ring structure, and more preferably have 5, 6, or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF3, —CN and the like. Cycloalkyls can be substituted in the same manner.

The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The terms "alkenyl" and "alkynyl", refer to unsaturated aliphatic groups analogous in length and possible substitution to the alkyls described above, but that contain at least one double or triple bond respectively.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. The terms "aroxy" and "aryloxy", as used interchangeably herein, can be represented by —O-aryl or O-heteroaryl, wherein aryl and heteroaryl are as defined below. The alkoxy and aroxy groups can be substituted as described above for alkyl.

"Aryl", as used herein, refers to C5-C10-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyrimidine, and the like. Those aryl groups having heteroatoms in the ring structure may also be referred to as "aryl heterocycles" or "heteroaromatics". The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF3, —CN, and combinations thereof.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1, 5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. One or more of the rings can be substituted as defined above for "aryl".

The term "aralkyl", as used herein, refers to an alkyl group substituted with an aryl group (e.g., an aromatic or heteroaromatic group).

The term "aralkyloxy" can be represented by —O-aralkyl, wherein aralkyl is as defined above.

The term "heteroatom" as used herein means an atom of any element other than carbon or hydrogen. Preferred heteroatoms are boron, nitrogen, oxygen, phosphorus, sulfur, and selenium. Other heteroatoms include silicon and arsenic.

As used herein, the term "nitro" means —NO2; the term "halogen" designates —F, —Cl, —Br, or —I; the term "sulfhydryl" means —SH; the term "hydroxyl" means —OH; and the term "sulfonyl" means —SO2-.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, C3-C20 cyclic, substituted C3-C20 cyclic, heterocyclic, substituted heterocyclic, amino acid, peptide, and polypeptide groups.

II. Compositions

A. Compounds

Compounds having the following NSC numbers: 309401, 80735, 123458, 157522, 159686, 379536, 50690, 55152, and 130801 are provided. These compounds bind to DHFR and inhibit DHFR activity. A preferred compound, NSC309401, is represented by Formula I (7-[(4-aminophenyl)methyl]-7Hpyrrolo[3,2-f]quinazoline-1,3-diamine) and is an antifolate with potent binding to the enzyme DHFR.

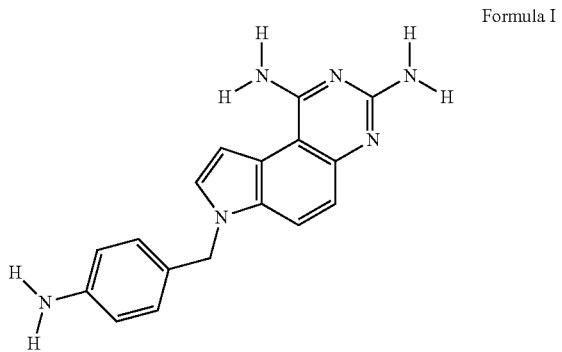 [SMILES: Nc1ccc(Cn2ccc3c4c(N)nc(N)nc4ccc32)cc1]

Formula I

Figure 3A:
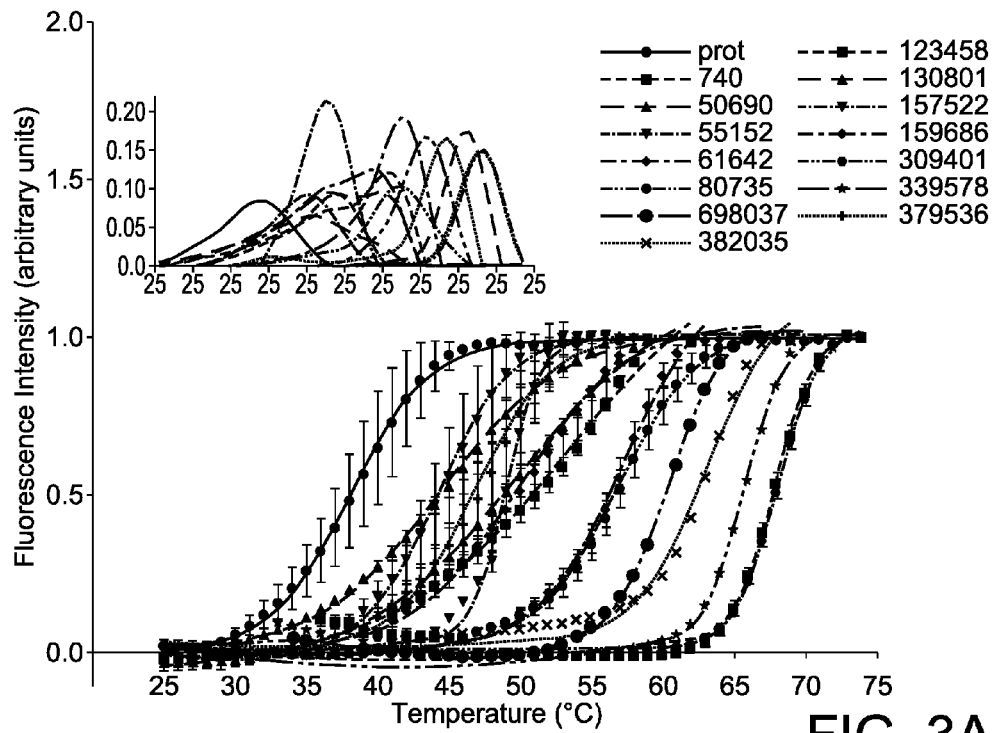
FIG. 3A shows the binding of 309401, 80735, 123458, 157522, 159686, 379536, 50690, 55152, and 130801 to DHFR assayed using a thermal shift assay (TSA) in a high-throughput screening (HTS) format on a 96 well-plate using quantitative real-time PCR equipment.

The binding of 309401, 80735, 123458, 157522, 159686, 379536, 50690, 55152, and 130801 to DHFR was assayed using a thermal shift assay (TSA) in a high-throughput screening (HTS) format on a 96 well-plate using quantitative real-time PCR equipment (FIG. 3A). The thermal shift assay is a method that is independent of the catalytic activity and is dependent on the structural stability of the enzyme, whereby, in the presence of the said compound, the thermal stability of the enzyme increased indicative of binding. The delta-$T_m$ (the difference in the midpoint of transition in the thermal melting curve between protein alone and protein with ligand) for NSC309401 was around 30 degrees Celsius that can be extrapolated to an approximate dissociation constant of 48 nM which is indicative of tight binding.

The compound can include a derivative of (7-[(4-aminophenyl)methyl]-7H-pyrrolo[3,2-f]quinazoline-1,3-diamine). Derivatives that do not diminish binding to the enzyme DHFR from *Escherichia coli* are preferred. The term "derivative" does not mean that the derivative is synthesized from the parent compound either as a starting material or intermediate, although this may be the case. The term "derivative" can include salts, prodrugs, or metabolites of the parent compound. Derivatives include compounds in which free amino groups in the parent compound have been derivatized to form amine hydrochlorides, p-toluene sulfonamides, benzoxycarboxamides, t-butyloxycarboxamides, thiourethane-type derivatives, trifluoroacetylamides, chloroacetylamides, or formamides. Derivatives include replacing one or more amino substituents or hydrogen groups with substituted or unsubstituted alkyl, aminoalkyl, aryl, or heteroaryl groups having from 1 to 30 carbon atoms.

The compound can have a structure according to Formula II or a derivative thereof, wherein n is an integer from 1 to 10, from 1 to 8, from 1 to 6, preferably from 1 to 4, most preferably 1; wherein each occurrence of $R^1$ is independently selected from the group consisting of H, hydroxyl, halide, and substituted and unsubstituted alkoxy, heteroalkoxy, alkyl, heteroalkyl, aryl, aryloxy, aralkyl, aralkyloxy, alkenyl, and alkynyl groups having from 1 to 30 carbon atoms, from 2 to 20 carbon atoms, or from 3 to 12 carbon atoms or, when attached to the same atom and taken together with the atom to which they are attached form a carbocycle or heterocycle having from 2 to 30, preferably from 3 to 12 carbon atoms; and wherein each occurrence of $R^2$ is independently selected from the group consisting of H, hydroxyl, halide, and substituted and unsubstituted alkoxy, heteroalkoxy, alkyl, heteroalkyl, aryl, aryloxy, aralkyl, aralkyloxy, alkenyl, and alkynyl groups having from 1 to 30 carbon atoms, from 2 to 20 carbon atoms. Exemplary alkyl groups include ethyl, propyl, butyl, hexyl, octyl, and decyl groups, as well as isomers thereof. Exemplary heteroalkyl groups include cyanobutyl and cyanopropyl groups. Exemplary alkoxy groups include methoxy, ethoxy, and butoxy groups.

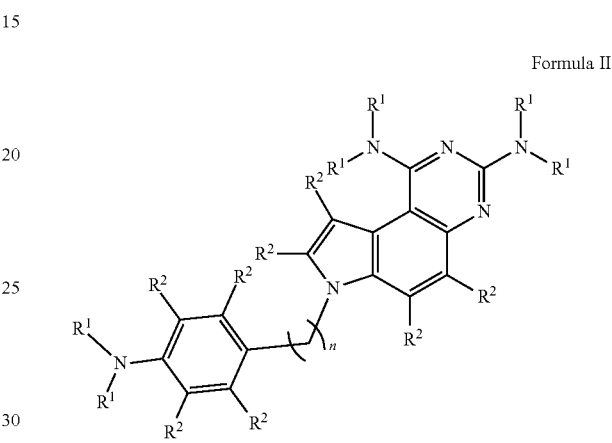

Formula II

1. Pharmaceutically Acceptable Salts

Also disclosed herein are pharmaceutically acceptable salts of the compound represented by Formula I, and the derivatives thereof as well as other compounds that were determined to bind DHFR. Examples of pharmaceutically acceptable salts include, but are not limited to mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, tolunesulfonic, naphthalenesulfonic, methanesulfonic, ethane disulfonic, oxalic, and isethionic salts.

The pharmaceutically acceptable salts of the compounds can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 20th ed., Lippincott Williams & Wilkins, Baltimore, Md., 2000, p. 704; and "Handbook of Pharmaceutical Salts:

Properties, Selection, and Use," P. Heinrich Stahl and Camille G. Wermuth, Eds., Wiley-VCH, Weinheim, 2002.

2. Intermediates

The compounds identified herein using virtual ligand screening can be used as a starting compound or intermediate compound to produce a final compound that has increased binding to an enzyme, for example DHFR, or increased inhibition of the enzyme, for example DHFR, relative to starting compound or intermediate compound. The compounds identified herein can be modified to increase bioavailability, increase half-life in the blood stream, increase solubility, increase hydrophilicity, increase hydrophobicity, or a combination thereof using conventional techniques.

The compounds can be modified to incorporate polar functional groups, such as the alcohol, amine, amide, carboxylic acid, sulfonic acid and phosphate groups, which either ionize or are capable of relatively strong intermolecular forces of attraction with water (hydrogen bonding), usually resulting in analogues with an increased water solubility. Acidic and basic groups are particularly useful, since these groups can be used to form salts, which would give a wider range of dosage forms for the final product. However, the formation of zwitterions by the introduction of either an acid group into a structure containing a base or a base group into a structure containing an acid group can reduce water solubility. Introduction of weakly polar groups, such as carboxylic acid esters, aryl halides and alkyl halides, will not significantly improve water solubility and can result in enhanced lipid solubility.

The incorporation of acidic residues into the compound is less likely to change the type of activity, but it can result in the analogue exhibiting hemolytic properties. Furthermore, the introduction of an aromatic acid group usually results in anti-inflammatory activity, whilst carboxylic acids with an alpha functional group may act as chelating agents. Basic water solubilizing groups have a tendency to change the mode of action, since bases often interfere with neurotransmitters and biological processes involving amines. However, their incorporation does mean that the analogue can be formulated as a wide variety of acid salts. Non-ionizable groups do not have the disadvantages of acidic and basic groups.

Groups that are bound directly to the carbon skeleton of the lead compound by less reactive C—C, C—O and C—N bonds are likely to be irreversibly attached to the lead structure. Groups that are linked to the compound by ester, amide, phosphate, sulfate and glycosidic bonds are more likely to be metabolized from the resulting analogue to reform the parent compound as the analogue is transferred from its point of administration to its site of action. Compounds with this type of solubilizing group are acting as prodrugs and so their activity is more likely to be the same as the parent compound. However, the rate of loss of the solubilizing group will depend on the nature of the transfer route, and this could affect the activity of the drug.

To preserve the type of activity exhibited by the compound, a water solubilizing group should be attached to a part of the structure that is not involved in the drug-receptor interaction. Consequently, the route used to introduce a new water solubilizing group and its position in the lead compound will depend on the relative reactivities of the compound and the rest of the molecule. Examples of water solubilizing structures and the routes used to introduce them into the lead structures. O-alkylation, N-alkylation, O-acylation and N-acylation reactions are used to introduce both acidic and basic groups. Acetylation methods use both the appropriate acid chloride and anhydride.

Examples of water solubilizing structures and the routes used to introduce them into lead compounds include but are not limited to phosphate acid halides for introducing phosphate groups into compounds. Structures containing hydroxy groups have been introduced by reaction of the corresponding monochlorinated hydrin and the use of suitable epoxides. Sulphonic acid groups may be introduced by either direct sulfonation or the addition of bisulfite to reactive C=C bonds.

B. Formulations

The compounds described herein can be formulated for enteral, parenteral, topical, or pulmonary administration. The compounds can be combined with one or more pharmaceutically acceptable carriers and/or excipients that are considered safe and effective and may be administered to an individual without causing undesirable biological side effects or unwanted interactions. The carrier is all components present in the pharmaceutical formulation other than the active ingredient or ingredients.

The compounds disclosed herein can also be formulated for use as a disinfectant, for example, in a hospital environment.

1. Parenteral Formulations

The compounds described herein can be formulated for parenteral administration.

For example, parenteral administration may include administration to a patient intravenously, intradermally, intraarterially, intraperitoneally, intralesionally, intracranially, intraarticularly, intraprostatically, intrapleurally, intratracheally, intravitreally, intratumorally, intramuscularly, subcutaneously, subconjunctivally, intravesicularly, intrapericardially, intraumbilically, by injection, and by infusion.

Parenteral formulations can be prepared as aqueous compositions using techniques known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, viscosity modifying agents, and combination thereof.

Suitable surfactants may be anionic, cationic, amphoteric or nonionic surface-active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water-soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

(a) Controlled Release Formulations

The parenteral formulations described herein can be formulated for controlled release including immediate release, delayed release, extended release, pulsatile release, and combinations thereof.

1. Nano- and Microparticles

For parenteral administration, the one or more compounds, and optional one or more additional active agents, can be incorporated into microparticles, nanoparticles, or combinations thereof that provide controlled release of the compounds and/or one or more additional active agents. In embodiments wherein the formulations contains two or more drugs, the drugs can be formulated for the same type of controlled release (e.g., delayed, extended, immediate, or pulsatile) or the drugs can be independently formulated for different types of release (e.g., immediate and delayed, immediate and extended, delayed and extended, delayed and pulsatile, etc.).

For example, the compounds and/or one or more additional active agents can be incorporated into polymeric microparticles, which provide controlled release of the drug(s). Release of the drug(s) is controlled by diffusion of the drug(s) out of the microparticles and/or degradation of the polymeric particles by hydrolysis and/or enzymatic degradation. Suitable polymers include ethylcellulose and other natural or synthetic cellulose derivatives.

Polymers, which are slowly soluble and form a gel in an aqueous environment, such as hydroxypropyl methylcellulose or polyethylene oxide, can also be suitable as materials for drug containing microparticles. Other polymers include, but are not limited to, polyanhydrides, poly(ester anhydrides), polyhydroxy acids, such as polylactide (PLA), polyglycolide (PGA), poly(lactide-co-glycolide) (PLGA), poly-3-hydroxybutyrate (PHB) and copolymers thereof, poly-4-hydroxybutyrate (P4HB) and copolymers thereof, polycaprolactone and copolymers thereof, and combinations thereof.

Alternatively, the drug(s) can be incorporated into microparticles prepared from materials which are insoluble in aqueous solution or slowly soluble in aqueous solution, but are capable of degrading within the GI tract by means including enzymatic degradation, surfactant action of bile acids, and/or mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including but not limited to fatty acid esters, fatty acid glycerides (mono-, di- and tri-glycerides), and hydrogenated fats. Specific examples include, but are not limited to hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes. Specific examples of waxes include beeswax, glycowax, castor wax, carnauba wax, paraffins and candelilla wax. As used herein, a wax-like material is defined as any material, which is normally solid at room temperature and has a melting point of from about 30 to 300° C.

In some cases, it may be desirable to alter the rate of water penetration into the microparticles. To this end, rate-controlling (wicking) agents can be formulated along with the fats or waxes listed above. Examples of rate-controlling materials include certain starch derivatives (e.g., waxy maltodextrin and drum dried corn starch), cellulose derivatives (e.g., hydroxypropylmethylcellulose, hydroxypropylcellulose, methylcellulose, and carboxymethylcellulose), alginic acid, lactose and talc. Additionally, a pharmaceutically acceptable surfactant (for example, lecithin) may be added to facilitate the degradation of such microparticles.

Proteins, which are water insoluble, such as zein, can also be used as materials for the formation of drug containing microparticles. Additionally, proteins, polysaccharides and combinations thereof, which are water-soluble, can be formulated with drug into microparticles and subsequently cross-linked to form an insoluble network. For example, cyclodextrins can be complexed with individual drug molecules and subsequently cross-linked.

2. Method of Making Nano- and Microparticles

Encapsulation or incorporation of drug into carrier materials to produce drug-containing microparticles can be achieved through known pharmaceutical formulation techniques. In the case of formulation in fats, waxes or wax-like materials, the carrier material is typically heated above its inciting temperature and the drug is added to form a mixture comprising drug particles suspended in the carrier material, drug dissolved in the carrier material, or a mixture thereof. Microparticles can be subsequently formulated through several methods including, but not limited to, the processes of congealing, extrusion, spray chilling or aqueous dispersion. In a preferred process, wax is heated above its melting temperature, drug is added, and the molten wax-drug mixture is congealed under constant stirring as the mixture cools. Alternatively, the molten wax-drug mixture can be extruded and spheronized to form pellets or beads. These processes are known in the art.

For some carrier materials it may be desirable to use a solvent evaporation technique to produce drug-containing microparticles. In this case drug and carrier material are co-dissolved in a mutual solvent and microparticles can subsequently be produced by several techniques including, but not limited to, forming an emulsion in water or other appropriate media, spray drying or by evaporating off the solvent from the bulk solution and milling the resulting material.

In some embodiments, drug in a particulate form is homogeneously dispersed in a water-insoluble or slowly water soluble material. To minimize the size of the drug particles within the composition, the drug powder itself may be milled to generate fine particles prior to formulation. The process of jet milling, known in the pharmaceutical art, can be used for this purpose. In some embodiments drug in a particulate form is homogeneously dispersed in a wax or wax like substance by heating the wax or wax like substance above its melting point and adding the drug particles while stirring the mixture. In this case a pharmaceutically acceptable surfactant may be added to the mixture to facilitate the dispersion of the drug particles.

The particles can also be coated with one or more modified release coatings. Solid esters of fatty acids, which are hydrolyzed by lipases, can be spray coated onto microparticles or drug particles. Zein is an example of a naturally water-insoluble protein. It can be coated onto drug containing microparticles or drug particles by spray coating or by wet granulation techniques. In addition to naturally water-insoluble materials, some substrates of digestive enzymes can be treated with cross-linking procedures, resulting in the formation of non-soluble networks. Many methods of cross-linking proteins, initiated by both chemical and physical means, have been reported. One of the most common methods to obtain cross-linking is the use of chemical cross-linking agents. Examples of chemical cross-linking agents include aldehydes (gluteraldehyde and formaldehyde), epoxy compounds, carbodiimides, and genipin. In addition to these cross-linking agents, oxidized and native sugars have been used to cross-link gelatin. Cross-linking can also be accomplished using enzymatic means; for example, transglutaminase has been approved as a GRAS substance for cross-linking seafood products. Finally, cross-linking can be initiated by physical means such as thermal treatment, UV irradiation and gamma irradiation.

To produce a coating layer of cross-linked protein surrounding drug containing microparticles or drug particles, a water-soluble protein can be spray coated onto the microparticles and subsequently cross-linked by the one of the methods described above. Alternatively, drug-containing microparticles can be microencapsulated within protein by coacervation-phase separation (for example, by the addition of salts) and subsequently cross-linked. Some suitable proteins for this purpose include gelatin, albumin, casein, and gluten.

Polysaccharides can also be cross-linked to form a water-insoluble network. For many polysaccharides, this can be accomplished by reaction with calcium salts or multivalent cations, which cross-link the main polymer chains. Pectin, alginate, dextran, amylose and guar gum are subject to cross-linking in the presence of multivalent cations. Complexes between oppositely charged polysaccharides can also be formed; pectin and chitosan, for example, can be complexed via electrostatic interactions.

(b) Injectable/Implantable Formulations

The compounds described herein can be incorporated into injectable/implantable solid or semi-solid implants, such as polymeric implants. In one embodiment, the compounds are incorporated into a polymer that is a liquid or paste at room temperature, but upon contact with aqueous medium, such as physiological fluids, exhibits an increase in viscosity to form a semi-solid or solid material. Exemplary polymers include, but are not limited to, hydroxyalkanoic acid polyesters derived from the copolymerization of at least one unsaturated hydroxy fatty acid copolymerized with hydroxyalkanoic acids. The polymer can be melted, mixed with the active substance and cast or injection molded into a device. Such melt fabrication require polymers having a melting point that is below the temperature at which the substance to be delivered and polymer degrade or become reactive. The device can also be prepared by solvent casting where the polymer is dissolved in a solvent and the drug dissolved or dispersed in the polymer solution and the solvent is then evaporated. Solvent processes require that the polymer be soluble in organic solvents. Another method is compression molding of a mixed powder of the polymer and the drug or polymer particles loaded with the active agent.

Alternatively, the compounds can be incorporated into a polymer matrix and molded, compressed, or extruded into a device that is a solid at room temperature. For example, the compounds can be incorporated into a biodegradable polymer, such as polyanhydrides, polyhydroalkanoic acids (PHAs), PLA, PGA, PLGA, polycaprolactone, polyesters, polyamides, polyorthoesters, polyphosphazenes, proteins and polysaccharides such as collagen, hyaluronic acid, albumin and gelatin, and combinations thereof and compressed into solid device, such as disks, or extruded into a device, such as rods.

The release of the one or more compounds from the implant can be varied by selection of the polymer, the molecular weight of the polymer, and/or modification of the polymer to increase degradation, such as the formation of pores and/or incorporation of hydrolyzable linkages. Methods for modifying the properties of biodegradable polymers to vary the release profile of the compounds from the implant are well known in the art.

2. Enteral Formulations

Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Formulations may be prepared using a pharmaceutically acceptable carrier. As generally used herein "carrier" includes, but is not limited to, diluents, preservatives, binders, lubricants, disintegrators, swelling agents, fillers, stabilizers, and combinations thereof.

Carrier also includes all components of the coating composition, which may include plasticizers, pigments, colorants, stabilizing agents, and glidants.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

"Diluents", also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

"Binders" are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

"Lubricants" are used to facilitate tablet manufacture. Examples of suitable lubricants include, but are not limited to, magnesium stearate, calcium stearate, stearic acid, glycerol behenate, polyethylene glycol, talc, and mineral oil.

"Disintegrants" are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

"Stabilizers" are used to inhibit or retard drug decomposition reactions, which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

(a) Controlled Release Enteral Formulations

Oral dosage forms, such as capsules, tablets, solutions, and suspensions, can for formulated for controlled release. For example, the one or more compounds and optional one or more additional active agents can be formulated into nanoparticles, microparticles, and combinations thereof, and encapsulated in a soft or hard gelatin or non-gelatin capsule or dispersed in a dispersing medium to form an oral suspension or syrup. The particles can be formed of the drug and a controlled release polymer or matrix. Alternatively, the drug particles can be coated with one or more controlled release coatings prior to incorporation in to the finished dosage form.

In another embodiment, the one or more compounds and optional one or more additional active agents are dispersed in a matrix material, which gels or emulsifies upon contact with an aqueous medium, such as physiological fluids. In the case of gels, the matrix swells entrapping the active agents, which are released slowly over time by diffusion and/or degradation of the matrix material. Such matrices can be formulated as tablets or as fill materials for hard and soft capsules.

In still another embodiment, the one or more compounds, and optional one or more additional active agents are formulated into a sold oral dosage form, such as a tablet or capsule, and the solid dosage form is coated with one or more controlled release coatings, such as a delayed release coatings or extended release coatings. The coating or coatings may also contain the compounds and/or additional active agents.

(1) Extended Release Dosage Forms

The extended release formulations are generally prepared as diffusion or osmotic systems, which are known in the art. A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename EUDRAGIT T®. In further preferred embodiments, the acrylic polymer comprises a mixture of two acrylic resin lacquers commercially available from Rohm Pharma under the tradenames EUDRAGIT® RL30D and EUDRAGIT® RS30D, respectively. EUDRAGIT® RL30D and EUDRAGIT® RS30D are copolymers of acrylic and methacrylic esters with a low content of quaternary ammonium groups, the molar ratio of ammonium groups to the remaining neutral (meth)acrylic esters being 1:20 in EUDRAGIT® RL30D and 1:40 in EUDRAGIT® RS30D. The mean molecular weight is about 150,000. EUDRAGIT® S-100 and EUDRAGIT® L-100 are also preferred. The code designations RL (high permeability) and RS (low permeability) refer to the permeability properties of these agents. EUDRAGIT® RL/RS mixtures are insoluble in water and in digestive fluids. However, multiparticulate systems formed to include the same are swellable and permeable in aqueous solutions and digestive fluids.

The polymers described above such as EUDRAGIT® RL/RS may be mixed together in any desired ratio in order to ultimately obtain a sustained-release formulation having a desirable dissolution profile. Desirable sustained-release multiparticulate systems may be obtained, for instance, from 100% EUDRAGIT® RL, 50% EUDRAGIT® RL and 50% EUDRAGIT T® RS, and 10% EUDRAGIT® RL and 90% EUDRAGIT® RS. One skilled in the art will recognize that other acrylic polymers may also be used, such as, for example, EUDRAGIT® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

(2) Delayed Release Dosage Forms

Delayed release formulations can be created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including EUDRAGIT® L30D-55 and L100-55 (soluble at pH 5.5 and above), EUDRAGIT® L-100 (soluble at pH 6.0 and above), EUDRAGIT® S (soluble at pH 7.0 and above, as a result of a higher degree of esterification), and EUDRAGITS® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

3. Topical Formulations

Suitable dosage forms for topical administration include creams, ointments, salves, sprays, gels, lotions, emulsions, and transdermal patches. The formulation may be formulated for transmucosal, transepithelial, transendothelial, or transdermal administration. The compounds can also be formulated for intranasal delivery, pulmonary delivery, or inhalation. The compositions may further contain one or more chemical penetration enhancers, membrane permeability agents, membrane transport agents, emollients, surfactants, stabilizers, buffers, and combination thereof.

In certain embodiments, it may be desirable to provide continuous delivery of one or more compounds to a patient in need thereof. For topical applications, repeated application can be done or a patch can be used to provide continuous administration of the compounds over an extended period of time "Buffers" are used to control pH of a composition. Preferably, the buffers buffer the composition from a pH of about 4 to a pH of about 7.5, more preferably from a pH of about 4 to a pH of about 7, and most preferably from a pH of about 5 to a pH of about 7. In a preferred embodiment, the buffer is triethanolamine.

"Emollients" are an externally applied agent that softens or soothes skin and are generally known in the art and listed in compendia, such as the "Handbook of Pharmaceutical Excipients", 4$^{th}$ Ed., Pharmaceutical Press, 2003. These include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In one embodiment, the emollients are ethylhexylstearate and ethylhexyl palmitate.

"Emulsifiers" are surface active substances which promote the suspension of one liquid in another and promote the formation of a stable mixture, or emulsion, of oil and water. Common emulsifiers are: metallic soaps, certain animal and vegetable oils, and various polar compounds. Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxypropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

"Penetration enhancers" are known in the art and include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocylic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols). Examples of these classes are known in the art.

"Preservatives" can be used to prevent the growth of fungi and microorganisms. Suitable antifungal and antimicrobial agents include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

"Surfactants" are surface-active agents that lower surface tension and thereby increase the emulsifying, foaming, dispersing, spreading and wetting properties of a product. Suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

(a) Emulsions

An emulsion is a preparation of one liquid distributed in small globules throughout the body of a second liquid. In particular embodiments, the non-miscible components of the emulsion include a lipophilic component and an aqueous component. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

The oil phase may consist at least in part of a propellant, such as an HFA propellant. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

A sub-set of emulsions are the self-emulsifying systems. These drug delivery systems are typically capsules (hard shell or soft shell) comprised of the drug dispersed or dissolved in a mixture of surfactant(s) and lipophilic liquids such as oils or other water immiscible liquids. When the capsule is exposed to an aqueous environment and the outer gelatin shell dissolves, contact between the aqueous medium and the capsule contents instantly generates very small emulsion droplets. These typically are in the size range of micelles or nanoparticles. No mixing force is required to generate the emulsion as is typically the case in emulsion formulation processes.

(b) Lotions

A lotion can contain finely powdered substances that are in soluble in the dispersion medium through the use of suspending agents and dispersing agents. Alternatively, lotions can have as the dispersed phase liquid substances that are immiscible with the vehicle and are usually dispersed by means of emulsifying agents or other suitable stabilizers. In one embodiment, the lotion is in the form of an emulsion having a viscosity of between 100 and 1000 centistokes. The fluidity of lotions permits rapid and uniform application over a wide surface area. Lotions are typically intended to dry on the skin leaving a thin coat of their medicinal components on the skin's surface.

(c) Creams

Creams may contain emulsifying agents and/or other stabilizing agents. In one embodiment, the formulation is in the form of a cream having a viscosity of greater than 1000 centistokes, typically in the range of 20,000-50,000 centistokes. Creams are often time preferred over ointments, as they are generally easier to spread and easier to remove.

The difference between a cream and a lotion is the viscosity, which is dependent on the amount/use of various oils and the percentage of water used to prepare the formulations. Creams are typically thicker than lotions, may have various uses and often one uses more varied oils/butters, depending upon the desired effect upon the skin. In a cream formulation, the water-base percentage is about 60-75% and the oil-base is about 20-30% of the total, with the other percentages being the emulsifier agent, preservatives and additives for a total of 100%.

(d) Ointments

Examples of suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

(e) Gels

Gels are semisolid systems containing dispersions of small or large molecules in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Suitable gelling agents include, but are not limited to, modified celluloses, such as hydroxypropyl cellulose and hydroxyethyl cellulose; Carbopol homopolymers and copolymers; and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents are typically selected for their ability to dissolve the drug. Other additives, which improve the skin feel and/or emolliency of the formulation, may also be incorporated. Examples of such additives include, but are not limited, isopropyl myristate, ethyl acetate, $C_{12}$-$C_{15}$ alkyl benzoates, mineral oil, squalane, cyclomethicone, capric/caprylic triglycerides, and combinations thereof.

(f) Foams

Foams consist of an emulsion in combination with a gaseous propellant. The gaseous propellant consists primarily of hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or may become approved for medical use are suitable. The propellants preferably are not hydrocarbon propellant gases, which can produce flammable or explosive vapors during spraying. Furthermore, the compositions preferably contain no volatile alcohols, which can produce flammable or explosive vapors during use.

4. Pulmonary Formulations

In one embodiment, the compounds are formulated for pulmonary delivery, such as intranasal administration or oral inhalation.

The respiratory tract is the structure involved in the exchange of gases between the atmosphere and the blood stream. The lungs are branching structures ultimately ending with the alveoli where the exchange of gases occurs. The alveolar surface area is the largest in the respiratory system and is where drug absorption occurs. The alveoli are covered by a thin epithelium without cilia or a mucus blanket and secrete surfactant phospholipids. The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchiole, which then lead to the ultimate respiratory zone, the alveoli, or deep lung. The deep lung, or alveoli, is the primary target of inhaled therapeutic aerosols for systemic drug delivery.

Pulmonary administration of therapeutic compositions including low molecular weight drugs has been observed, for example, beta-androgenic antagonists to treat asthma. Other therapeutic agents that are active in the lungs have been administered systemically and targeted via pulmonary absorption. Nasal delivery is considered to be a promising technique for administration of therapeutics for the following reasons: the nose has a large surface area available for drug absorption due to the coverage of the epithelial surface by numerous microvilli, the sub epithelial layer is highly vascularized, the venous blood from the nose passes directly into the systemic circulation and therefore avoids the loss of drug by first-pass metabolism in the liver, it offers lower doses, more rapid attainment of therapeutic blood levels, quicker onset of pharmacological activity, fewer side effects, high total blood flow per cm3, porous endothelial basement membrane, and it is easily accessible.

Carriers for pulmonary formulations can be divided into those for dry powder formulations and for administration as solutions. Aerosols for the delivery of therapeutic agents to the respiratory tract are known in the art. Aerosols can be produced using standard techniques, such as ultrasonication or high-pressure treatment. For administration via the upper respiratory tract, the formulation can be formulated into a solution, e.g., water or isotonic saline, buffered or unbuffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2. One skilled in the art can readily determine a suitable saline content and pH for an innocuous aqueous solution for nasal and/or upper respiratory administration.

Preferably, the aqueous solution is water, physiologically acceptable aqueous solutions containing salts and/or buffers, such as phosphate buffered saline (PBS), or any other aqueous solution acceptable for administration to an animal or human. Such solutions are well known to a person skilled in the art and include, but are not limited to, distilled water, de-ionized water, pure or ultrapure water, saline, phosphate-buffered saline (PBS). Other suitable aqueous vehicles include, but are not limited to, Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

Solvents that are low toxicity organic (i.e. nonaqueous) class 3 residual solvents, such as ethanol, acetone, ethyl acetate, tetrahydrofuran, ethyl ether, and propanol may be used for the formulations. The solvent is selected based on its ability to readily aerosolize the formulation. The solvent should not detrimentally react with the compounds. An appropriate solvent should be used that dissolves the compounds or forms a suspension of the compounds. The solvent should be sufficiently volatile to enable formation of an aerosol of the solution or suspension. Additional solvents or aerosolizing agents, such as freons, can be added as desired to increase the volatility of the solution or suspension.

In one embodiment, compositions may contain minor amounts of polymers, surfactants, or other excipients well known to those of the art. In this context, "minor amounts" means no excipients are present that might affect or mediate uptake of the compounds in the lungs and that the excipients that are present are present in amount that do not adversely affect uptake of compounds in the lungs.

Dry lipid powders can be directly dispersed in ethanol because of their hydrophobic character. For lipids stored in organic solvents such as chloroform, the desired quantity of solution is placed in a vial, and the chloroform is evaporated under a stream of nitrogen to form a dry thin film on the surface of a glass vial. The film swells easily when reconstituted with ethanol. To fully disperse the lipid molecules in the organic solvent, the suspension is sonicated. Nonaqueous suspensions of lipids can also be prepared in absolute ethanol using a reusable PART LC Jet+ nebulizer (PARI Respiratory Equipment, Monterey, Calif.).

Dry powder formulations ("DPFs") with large particle size have improved flowability characteristics, such as less aggregation, easier aerosolization, and potentially less phagocytosis. Dry powder aerosols for inhalation therapy are generally produced with mean diameters primarily in the range of less than 5 microns, although a preferred range is between one and ten microns in aerodynamic diameter. Large "carrier" particles (containing no drug) have been co-delivered with therapeutic aerosols to aid in achieving efficient aerosolization among other possible benefits.

Polymeric particles may be prepared using single and double emulsion solvent evaporation, spray drying, solvent extraction, solvent evaporation, phase separation, simple and complex coacervation, interfacial polymerization, and other methods well known to those of ordinary skill in the art. Particles may be made using methods for making microspheres or microcapsules known in the art. The preferred methods of manufacture are by spray drying and freeze drying, which entails using a solution containing the surfactant, spraying to form droplets of the desired size, and removing the solvent.

The particles may be fabricated with the appropriate material, surface roughness, diameter and tap density for localized delivery to selected regions of the respiratory tract such as the deep lung or upper airways. For example, higher density or larger particles may be used for upper airway delivery. Similarly, a mixture of different sized particles, provided with the same or different EGS may be administered to target different regions of the lung in one administration.

Formulations for pulmonary delivery include unilamellar phospholipid vesicles, liposomes, or lipoprotein particles. Formulations and methods of making such formulations containing nucleic acid are well known to one of ordinary skill in the art. Liposomes are formed from commercially available phospholipids supplied by a variety of vendors including Avanti Polar Lipids, Inc. (Birmingham, Ala.). In one embodiment, the liposome can include a ligand molecule specific for a receptor on the surface of the target cell to direct the liposome to the target cell.

5. Disinfecting Formulations

The compounds can be formulated into cleaning formulations. The cleaning formulations are highly efficacious for household cleaning applications (e.g., hard surfaces like floors, countertops, tubs, dishes and softer cloth materials like clothing, sponges, paper towels, etc.), personal care applications (e.g. lotions, shower gels, soaps, shampoos, wipes) and industrial and hospital applications (e.g., sterilization of instruments, medical devices, gloves). These formulations are efficacious for cleaning surfaces which are infected or contaminated with Gram negative bacteria, Gram positive bacteria and fungi.

The compounds disclosed herein can be formulated into a solution in a suitable solvent for administration in a spray bottle, the compounds can be formulation as an aerosol, a foam, suitable for spraying onto surfaces, of imbibed into a suitable cloth suitable for wiping down a surface to be disinfected. Methods for making formulations for use as a disinfectant in the forms disclosed herein are known in the art.

One embodiment provides NSC309401 or a derivative thereof in a composition containing a pH dye indicator and an alkaline substance. The pH indicator dye indicates what surface has been disinfected and ensures that a sufficient time has passed to disinfect the surface. See for example, U.S. Publication No. 20140057987, which is incorporated by reference in its entirety.

Cleaning formulations can include the compounds and an acceptable carrier. The carrier can be in a wide variety of forms. For example, the carrier may be an aqueous-based solution or cleanser, an alcohol-based solution or gel or an emulsion carrier, including, but not limited to, oil-in-water, water-in-oil, water-in-oil-in-water, and oil-in-water-in-silicone emulsions. The carrier solution containing the compound(s) can be applied directly to the surface to be treated or delivered via a suitable substrate.

The cleaning formulations can be formulated for use on the skin. In these embodiments the compounds can be formulate in a dermatologically acceptable carrier. The dermatologically acceptable carriers can also be, for example, formulated as alcohol or water based hand cleansers, toilet bars, liquid soaps, shampoos, bath gels, hair conditioners, hair tonics, pastes, or mousses.

Cleaning formulations can contain one or more surfactants. The surfactant is suitably selected from anionic, nonionic, zwitterionic, amphoteric and ampholytic surfactants, as well as mixtures of these surfactants. Such surfactants are well known to those skilled in the detergency art. Nonlimiting examples of possible surfactants include isoceteth-20, sodium methyl cocoyl taurate, sodium methyl oleoyl taurate, and sodium lauryl sulfate. Examples of a broad variety of additional surfactants are described in McCutcheon's Detergents and Emulsifiers. North American Edition (1986), published by Allured Publishing Corporation. The cleansing formulations can optionally contain, at their art-established levels, other materials which are conventionally used in cleansing formulations.

Additional carriers suitable for the cleaning formulations may include various substrate-based products. In such instances, the present formulations may be impregnated into or onto the substrate products and may be allowed to remain wet or may be subjected to a drying process. For instance, suitable carriers include, but are not limited to, dry and wet wipes suitable for personal care and household use (e.g., nonwoven baby wipes, household cleaning wipes, surgical preparation wipes, etc.); diapers; infant changing pads; dental floss; personal care and household care sponges or woven cloths (e.g., washcloths, towels, etc.); tissue-type products (e.g. facial tissue, paper towels, etc.); and disposable garments (e.g., gloves, smocks, surgical masks, infant bibs, socks, shoe inserts, etc.). Cleaning formulations can be incorporated into various household care products including, but not limited to, hard surface cleaners (e.g., disinfectant sprays, liquids, or powders); dish or laundry detergents (liquid or solid), floor waxes, glass cleaners, etc.

Exemplary carriers can include aqueous solutions, e.g. having from about 0% to about 98.8%, by weight of the composition, of water. Additionally, carriers may contain an aqueous alcohol solution. The amount of alcohol present in the alcohol solution will vary depending on the type of product in which the composition is incorporated, i.e. say a wipe where the preferred amount of alcohol present would be from about 0% to about 25% whereas a hand sanitizer preferably contains from about 60% to about 95%, of alcohol. Therefore, suitable dermatologically acceptable alcohol solutions or gels may contain from about 0% to about 95%, by weight of the composition, of an alcohol.

Alcohols suitable for inclusion in the alcohol solutions of the carrier include, but are not limited to, monohydric alcohols, dihydric alcohols, and combinations thereof. More preferred alcohols are selected from the group consisting of monohydric linear or branched C2-C18 alcohols. The most preferred alcohols are selected from the group consisting of ethanol, isopropanol, n-propanol, butanol, and combinations thereof. The cleaning formulations which contain a an alcohol solution may be anhydrous or water containing.

Thickeners can be added to the water or alcohol based to form a gel. Examples of suitable thickeners include, but are not limited to, naturally-occurring polymeric materials such as sodium alginate, xanthan gum, quince seed extract, tragacanth gum, starch and the like, semi-synthetic polymeric materials such as cellulose ethers (e.g. hydroxyethyl cellulose, methyl cellulose, carboxymethyl cellulose, hydroxy propylmethyl cellulose), polyvinylpyrrolidone, polyvinylalcohol, guar gum, hydroxypropyl guar gum, soluble starch, cationic celluloses, cationic guars and the like and synthetic polymeric materials such as carboxyvinyl polymers, polyvinylpyrrolidone, polyvinyl alcohol, polyacrylic acid polymers, polymethacrylic acid polymers, polyvinyl acetate polymers, polyvinyl chloride polymers, polyvinylidene chloride polymers and the like. Inorganic thickeners may also be used such as aluminum silicates, such as, for example, bentonites, or a mixture of polyethylene glycol and polyethylene glycol stearate or distearate.

The cleaning formulations can contain, in addition to the compounds described above, one or more antimicrobial or antifungal agents. Such agents are capable of destroying microbes, preventing the development of microbes or preventing the pathogenic action of microbes. Examples of additional antimicrobial and antifungal agents include β-lactam drugs, quinolone drugs, ciprofloxacin, norfloxacin, tetracycline, erythromycin, amikacin, 2,4,4'-trichloro-2'-hydroxy diphenyl ether (Triclosan®), phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, ketaconazole, amanfadine hydrochloride, amanfadine sulfate, octopirox, parachlorometa xylenol, nystatin, tolnaftate, pyrithiones (especially zinc pyrithione which is also known as ZPT), dimethyldimethylol hydantoin (Glydant®), methylchloroisothiazolinone/methylisothiazolinone (Kathon CG®), sodium sulfite, sodium bisulfite, imidazolidinyl urea (German 115®), diazolidinyl urea (Germaill II®), benzyl alcohol, 2-bromo-2-nitropropane-1,3-diol (Bronopol®), formalin (formaldehyde), iodopropenyl butylcarbamate (Polyphase P100®), chloroacetamide, methanamine, methyldibromonitrile glutaronitrile (1,2-Dibromo-2,4-dicyanobutane or Tektamer®), glutaraldehyde, 5-bromo-5-nitro-1,3-dioxane (Bronidox®), phenethyl alcohol, o-phenylphenol/sodium o-phenylphenol, sodium hydroxymethylglycinate (Suttocide A®), polymethoxy bicyclic oxazolidine (Nuosept C®), dimethoxane, thimersal dichlorobenzyl alcohol, captan, chloφhenenesin, dichlorophene, chlorbutanol, glyceryl laurate, halogenated diphenyl ethers like trichloro-2'-hydroxydiphenyl ether (Triclosan® or TCS), 2,2'-dihydroxy-5,5'-dibromo-diphenyl ether, phenolic compounds like phenol, 2-methyl phenol, 3-methyl phenol, 4-methyl phenol, 4-ethyl phenol, 2,4-dimethyl phenol, 2,5-dimethyl phenol, 3,4-dimethyl phenol, 2,6-dimethyl phenol, 4-n-propyl phenol, 4-n-butyl phenol, 4-n-amyl phenol, 4-tert-amyl phenol, 4-n-hexyl phenol, 4-n-heptyl phenol, mono- and poly-alkyl and aromatic halophenols such as p-chlorophenol, methyl p-chlorophenol, ethyl p-chlorophenol, n-propyl p-chlorophenol, n-butyl p-chlorophenol, n-amyl p-chlorophenol, sec-amyl p-chlorophenol, n-hexyl p-chlorophenol, cyclohexyl p-chlorophenol, n-heptyl p-chlorophenol, n-octyl p-chlorophenol, o-chlorophenol, methyl o-chlorophenol, ethyl o-chlorophenol, n-propyl o-chlorophenol, n-butyl o-chlorophenol, n-amyl o-chlorophenol, tert-amyl o-chlorophenol, n-hexyl o-chlorophenol, n-heptyl o-chlorophenol, o-benzyl p-chlorophenol, o-benzyl-m-methyl p-chlorophenol, o-benzyl-m, m-dimethyl p-chlorophenol, o-phenylethyl p-chlorophenol, o-phenylethyl-m-methyl p-chlorophenol, 3-methyl p-chlorophenol, 3,5-dimethyl p-chlorophenol, 6-ethyl-3-methyl p-chlorophenol, 6-n-propyl-3-methyl p-chlorophenol, 6-iso-propyl-3-methyl p-chlorophenol, 2-ethyl-3,5-dimethyl p-chlorophenol, 6-sec-butyl-3-methyl p-chlorophenol, 2-iso-propyl-3,5-dimethyl p-chlorophenol, 6-diethylmethyl-3-methyl p-chlorophenol, 6-iso-propyl-2-ethyl-3-methyl p-chlorophenol, 2-sec-amyl-3,5-dimethyl p-chlorophenol, 2-diethylmethyl-3,5-dimethyl p-chlorophenol, 6-sec-octyl-3-methyl p-chlorophenol, p-chloro-m-cresol, p-bromophenol, methyl p-bromophenol, ethyl p-bromophenol, n-propyl p-bromophenol, n-butyl p-bromophenol, n-amyl p-bromophenol, sec-amyl p-bromophenol, n-hexyl p-bromophenol, cyclohexyl p-bromophenol, o-bromophenol, test-amyl o-bromophenol, n-hexyl o-bromophenol, n-propyl-m,m-dimethyl o-bromophenol, 2-phenyl phenol, 4-chloro-2-methyl phenol, 4-chloro-3-methyl phenol, 4-chloro-3,5-dimethyl phenol, 2,4-dichloro-3,5-dimethylphenol, 3,4,5,6-terabromo-2-methylphenol, 5-methyl-2-pentylphenol, 4-isopropyl-3-methylphenol, para-chloro-meta-xylenol (PCMX), chlorothymol, 5-chloro-2-hydroxydiphenylmethane, resorcinol and its derivatives including methyl resorcinol, ethyl resorcinol, n-propyl resorcinol, n-butyl resorcinol, n-amyl resorcinol, n-hexyl resorcinol, n-heptyl resorcinol, n-octyl resorcinol, n-nonyl resorcinol, phenyl resorcinol, benzyl resorcinol, phenylethyl resorcinol, phenylpropyl resorcinol, p-chlorobenzyl resorcinol, 5-chloro 2,4-dihydroxydiphenyl methane, 4'-chloro 2,4-dihydroxydiphenyl methane, 5-bromo 2,4-dihydroxydiphenyl methane, and 4'-bromo 2,4-dihydroxydiphenyl methane, bisphenolic compounds like 2,2'-methylene bis (4-chlorophenol), 2,2'-methylene bis(3,4,6-trichlorophenol), 2,2'-methylene bis(4-chloro-6-bromophenol), bis(2-hydroxy-3,5-dichlorophenyl) sulphide, and bis(2-hydroxy-5-chlorobenzyl)sulphide, benzoic esters (parabens) like methylparaben, propylparaben, butylparaben, ethylparaben, isopropylparaben, isobutylparaben, benzylparaben, sodium methylparaben, and sodium propylparaben, halogenated carbanilides (e.g., 3,4,4'-trichlorocarbanilides (Triclocarban® or TCC), 3-trifluoromethyl-4,4'-dichlorocarbanilide, 3,3',4-trichlorocarbanilide, etc.), cationic actives such as benzalkonium chloride, and clotrimazole. Another class of antimicrobial agents (specifically antibacterial agents) which are useful in the present invention, are the so-called "natural" antibacterial actives, referred to as natural essential oils. Typical natural essential oil antibacterial actives include oils of anise, lemon, orange, rosemary, wintergreen, thyme, lavender, cloves, hops, tea tree, citronella, wheat, barley, lemongrass, cedar leaf, cedarwood, cinnamon, fleagrass, geranium, sandalwood, violet, cranberry, eucalyptus, vervain, peppermint, gum benzoin, basil, fennel, fir, balsam, menthol, ocmea origanum, Hydastis carradensis, Berberidaceae daceae, Ratanhiae and Curcuma longa.

The cleaning formulations may be packaged in a variety of suitable packaging known to those skilled in the art. The liquid formulations may desirably be packaged in manually operated spray dispensing containers, which are usually made of synthetic organic polymeric plastic materials. Accordingly, disinfecting formulations containing the compounds described herein and packaged in a spray dispenser, preferably in a trigger spray dispenser or a pump spray dispenser, are envisioned. Spray-type dispensers allow to uniformly apply to a relatively large area of a surface to be disinfected a liquid cleaning formulations described herein.

The disclosed compounds, for example NSC309401 or a derivative thereof can be impregnated into a nonwoven absorbent wipe. Disinfectant wet wipes are also disclosed for example in U.S. Pat. No. 8,563,017.

The disclosed compounds, for example NSC309401 or a derivative thereof can be in an aqueous foam with a special surfactant system capable of generating a foam. See U.S. Pat. No. 8,097,265, U.S. Pat. No. 5,891,922 and U.S. Pat. No. 4,889,645.

The disclosed compounds, for example NSC309401 or a derivative thereof can be in a pressurized spray aerosol. See also, U.S. Publication No. 20010053333 which discloses a liquid flash-dry aerosol disinfectant composition with a flash vaporization component and an effective amount of an antimicrobial agent.

It is within the abilities of one of ordinary skill in the art to determine the effective amount of the compounds disclosed herein to include in an aerosol, foam, solution or disinfectant cloth for the purpose of sterilizing for example, high risk hospital surfaces.

III. Compound Identification

A. Virtual Ligand Screening

Therapeutic compounds provided herein were identified using virtual ligand screening. Traditional experimental approaches to drug discovery rely on two different strategies (Drews, *Science,* 287(5460):1960-1964 (2000)). The first selects a reliable therapeutic target that might be essential for an organism's or cell's survival, and then, using chemical library screening, potential leads that bind to and modulate the activity of the target in vitro and subsequently, in vivo, are identified. The second approach tests small molecules on animal disease models or cell cultures (called phenotypic screening), and once activity is gleaned, the protein target is experimentally identified by target deconvolution (Terstappen, et al., *Nature reviews Drug discovery*, 6(11):891-903. (2007)). Both approaches have contributed to the discovery of new drugs despite suffering from substantial disadvantages of high cost and time. Fragment-based drug discovery approaches have recently gained prominence as a distinct and complementary approach to drug discovery (Ham, et al., *B Kor Chem Soc.*, 23(10):1371-1372 (2002)). Integration of a robust VLS methodology with experimental HTS approaches constitutes one of the many methods that might accelerate the drug discovery process (Bajorath, et al., *Nature reviews Drug discovery*, 1(11):882-894 (2002)).

Despite its current limitations, virtual ligand screening (VLS) may be employed as a possible first step in drug discovery (Reddy, et al., *Current protein & peptide science*, 8(4):329-351. (2007)). It not only aids in the selection of an appropriate protein target but also narrows down the chemical space that is experimentally screened to arrive at significant protein-ligand interactions. In practice, both ligand- and structure-based VLS approaches (Kroemer, et al., *Current Protein & Peptide Science*, 8(4):312-328 (2007)) have been used. The principal disadvantage of a ligand-based approach is the need for a priori knowledge of a set of ligands known to bind to the target (Hert, et al., *J. Chem. Info. & Model.*, 46(2):462-470 (2006)). Structure-based approaches require a high-resolution structure of the target; this situation typically only holds for a minority of proteins in a given proteome Klebe, et al., *Drug Discovery Today*, 11(13-14):580-594 (2006)). To overcome these limitations, ligand homology modeling (LHM) was developed to predict ligands that bind to the protein target (Brylinski, et al., *PNAS*, (105(1):129-134); Wass, et al., *Nucleic Acids Research*, 38(Web Server issue):W469-473 (2010); and Brylinski, et al., *PLoS Computational Biology*, 5(6):e1000405 (2009)). LHM relies on the fact that evolutionarily distant proteins share functional overlap and their ligand-binding information provides diverse bound ligands that can be employed in a general VLS approach. Thus, it does not suffer from the limitations of quantitative structure-activity relationship (QSAR)-based approaches. In large scale benchmarking, the FINDSITE$^{comb}$ LHM approach exhibited significant performance advantages over traditional approaches in terms of enrichment factor, speed, and insensitivity as to whether experimental or predicted protein structures are used (Zhou, et al., *J. Chem., Info. & Model.*, 53(1):230-240 (2013)).

A reliable and fast method that tests VLS predictions and identify hits could accelerate the drug-discovery process. This alleviates the inherent complexity of treating diseases due to cross-reactivity and could address the rapid evolution of resistance to available drugs by pathogenic microbes. In the present study the thermal shift assay methodology was used to assess the predictions from VLS (Niesen, et al., *Nature Protocols*, 2(9):2212-2221. (2007)). The methodology is an inexpensive way to assess the binding of small-molecules by the stability they confer on thermal denaturation of the protein target of interest. Upon thermal denaturation, the hydrophobicity of proteins increases leading to an increase in fluorescence of an extrinsic fluorophore reporter dye. This method is amenable to miniaturization and can screen hundreds of molecules simultaneously for their ability to bind to the protein target of interest.

B. Validation of the FINDSITE$^{comb}$ VLS Methodology

The data provided herein describe the large-scale experimental validation of the FINDSITE$^{comb}$ VLS methodology and demonstrate that the approach is applicable to a wide variety of proteins. In contrast, previous instances of VLS coupled to experimental screening of ligands reported in the literature mostly concentrate on either a single enzyme or a single enzyme family (Bowers, et al., *Chemistry & Biology*, 17(5):471-482 (2010), Polgar, et al., *J. of Med Chem*, 48(25):7946-7959 (2005); Babaoglu, et al., *J. Med. Chem.*, 51(8):2502-2511 (2008); Gruneberg, et al., *J. of Med Chem.*, 45(17):3588-3602 (2002); Gozalbes, et al., *J. of Med Chem.*, 51(11):3124-3132 (2008) and Doman, et al., *J. of Med Chem.*, 45(11):2213-2221 (2002). FINDSITE$^{comb}$, being a hybrid of structure-based and ligand-based VLS approaches, has many advantages: It identifies a structurally diverse set of ligands as potential hits, retains the speed of traditional ligand-based approaches, and removes the requirement of traditional structure-based approaches that a high-resolution structure of the protein target of interest be solved. Thus, ~75% of a given proteome is accessible to this VLS methodology. This affords the possibility not only of identifying novel hits, but also for repurposing FDA approved drugs, and concomitantly suggesting possible drug side effects.

Demonstration of the methodology on a diverse set of proteins with differing folds shows that the method is a general and effective approach to discovering novel protein-ligand binding interactions. The primary success rates of 4%-47% are dramatic when compared to rates reported in the literature. Since only a tiny fraction of the protein/ligand binding predictions were assessed experimentally (20-50 of the top ranked predictions from FINDSITE$^{comb}$), these success rates are even more significant than the raw numbers would suggest. For instance, in another study describing the HTS of a diverse library of 50,000 small-molecules against *E. coli* DHFR, the primary hit rate was 0.12% whereas 47% of the 32 molecules predicted by FINDSITE$^{comb}$ bind with µM affinities or better. Indeed, the finding that many ligands have $K_D$s in the nM and µM range is encouraging. For three different proteins, novel nM binders were identified.

Demonstration of antibacterial and cytotoxic activity by some of these compounds further suggests that the present methodology is a promising approach to identify novel hits and could help enrich the drug discovery pipeline.

Not only has a methodological advance been demonstrated, but also the results hold possible medical significance. Several interesting hits have been identified that might represent starting scaffolds for drug design for a number of clinically important protein targets. For example, DHFR, a pivotal enzyme in the nucleotide biosynthetic pathway in *E. coli* evolves resistance to available inhibitors by several mechanisms (Schnell, et al., *Annual Rev Biophys., Biomel. Struc.*, 33:119-140 (2004); Schimke, et al., *Science*, 202(4372):1051-1055 (1978); and Lynch, et al., *J. Infect. Dis.*, 197(11):1598-1604 (2008). This is a major problem because drug-resistant *E. coli* causes the highest number of infections in hospitalized patients. Thus, there is an urgent need to identify novel potent inhibitors of DHFR. In that regard, the current study provides nine novel structurally diverse small-molecule binders with apparent affinities ranging from nM to µM that are interesting hits that could be developed as lead molecules for *E. coli* DHFR inhibition. These nine molecules include NSC numbers 309401, 80735, 123458, 157522, 159686, 379536, 50690, 55152, and 130801. By assessing the potential of these ligands against a diverse set of drug-resistant microbial strains and colon cancer cells, the range of effectiveness of these compounds was established. A potent antibacterial and 7 molecules with cytotoxic effect against HCT-116 colon carcinoma cell line were found. This information can be exploited in designing species-specific inhibitors. Yet another example are the pathogens *P. falciparum*, which causes malignant malaria in humans, and *P. knowlesi*, implicated in an emergent form of malaria that can infect humans (McCutchan, et al., *Emerg. Infect. Dis.*, 14(11):1750-1752 (2008). Rapid evolution of resistance to known antimalarials is a major issue (Wongsrichanalai, et al., *The Lancet Infect. Dis.*, 2(4):209-218. (2002). The present study yielded 8 hits to three different enzymes that carry out critical processes of ubiquitin-mediated post-translational modification (UCE) (Poets, et al., *PloS One*, 3(6):e2386 (2008)), oxidative protection of the parasite during its intraerythrocytic stages (TP2) (Boucher, et al., *Mol. Microbiol*, 61(4):948-959 (2006)) and histone transport & chromatin assembly (NAP1) (Navadgi, et al., *J. Biol., Chem.*, 281(25):16978-16984 (2006)), in the pathogen. Finally, four distinct target proteins representing members of three families, tRNA synthetases, phosphatases and kinases implicated in diseases such as cancer (Park, et al., *PNAS.*, 105(32):11043-11049 (2008); Alonso, et at, *Cell*, 117(6):699-711 (2004) and Taylor, et al., *Biochimica et Biophysica Acta*, 1784(1):16-26 (2008)) were examined with 24 novel protein-ligand binding interactions reported. Interestingly, these studies also identified unanticipated binding interactions of well-known drugs with alternative targets. Sunitinib, a well-documented inhibitor of receptor tyrosine kinases, binds to TrpRS with high-affinity. This reinforces the belief that drug molecules, at least partly, work by interfering with the function of multiple targets within the cellular milieu. It is well known that developing a new drug is a time consuming and expensive process that can take 12-15 years. Such off-target interactions could be exploited towards repurposing available drugs for alternative protein targets, thus reducing the cost and time duration of drug-discovery.

IV. Method of Using the Compositions

NSC309401, 80735, 123458, 157522, 159686, 379536, 50690, 55152, 130801, derivatives thereof and combinations thereof can be administered to a subject in need thereof in an effective amount to treat a microbial infection. The microbial infection can be an infection from bacteria, fungi, or a combination thereof. In a preferred embodiment the infection is the result of multi-drug resistant bacterium or fungus. In other embodiments, the compounds disclosed herein can also be used as a sterilizing agent. The sterilizing agent can be used in high-risk environments such as in hardware from hospitals or healthcare facilities. In still other embodiments, NSC309401 or a derivative thereof can be used to treat a hyperproliferative condition, for example to inhibit tumor growth.

A. Methods of Treatment
1. Infections
NSC309401, 80735, 123458, 157522, 159686, 379536, 50690, 55152, 130801, derivatives thereof and combinations thereof can be administered as described above in an amount effective to inhibit DHFR in microbes infecting a subject, preferably a human subject. Inhibition of DHFR in the microbe inhibits growth and reproduction of the microbe and thereby helps reduce or inhibit the infection. The infection can be systemic or local. The infection can be an infection of the skin, eye, throat, nose, ear or of any organ including but not limited to lungs, intestine, heart, brain, and liver. The infection can be an abscess or a wound.

In certain embodiments, it may be desirable to provide continuous delivery of one or more compounds to a patient in need thereof. For intravenous or intraarterial routes, this can be accomplished using drip systems, such as by intravenous administration. For topical applications, repeated application can be done or a patch can be used to provide continuous administration of the compounds over an extended period of time.

2. Microbes
The infection to be treated can be caused by any microbe that expresses DHFR. Exemplary microbes that can be inhibited with the disclosed compounds include, but are not limited to, methicillin-resistant *Staphylococcus aureus*, *Enterococcus faecalis* and vancomycin-resistant strains of *Enterococcus faecium* (VREF) or fungi such as *Candida albicans*

Other bacteria that can be treated include, but are not limited to *Antinomies, Anabaena, Bacillus, Bacteroides, Bdellovibrio, Bordetella, Borrelia, Campylobacter, Caulobacter, Chlamydia, Chlorobium, Chromatium Clostridium, Corynebacterium, Cytophaga, Deinococcus, Escherichia, Francisella, Halobacterium, Heliobacter, Haemophilus, Hemophilus influenza* type B (HIB), *Hyphomicrobium, Legionella, Leptspirosis, Listeria, Meningococcus* A, B and C, *Methanobacterium, Micrococcus, Myobacteriwn, Mycoplasma, Myxococcus, Neisseria, Nitrobacter, Oscillatoria, Prochloron, Proteus, Pseudomonas, Phodospirillutn, Rickettsia, Salmonella, Shigella, Spirillum, Spirochaeta, Staphylococcus, Streptococcus, Streptomyces, Sulfolobus, Thermoplasma, Thiobacillus*, and *Treponema, Vibrio*, and *Yersinia*.

The compositions may be used to infections of microbes resistant to vancomycin. In this embodiment, the compositions disclosed herein can be used for treatment of infections resulting from vancomycin resistant enterococci. More than 95% of VRE recovered in the United States are *E. faecium*. Rice, *Emerg Infect. Dis.* 7(2):183-187 (2001).

For example, the compositions are useful for treatment of nosocomial (hospital-acquired) infections caused by vancomycin-resistant strains of *Enterococcus faecalis* (VREF). *Enterococcus* is an anaerobic bacterial genus that is a commensal inhabitant of the human intestine. Because of their intrinsic drug resistance, enterococci are an important pathogen in the hospital environment and are a major cause of nosocomial (health care-associated) infections. Although colonization with resistant strains is the norm, physically debilitated patients can develop endocarditis, surgical wound, urinary tract, or bloodstream infections. The rapid increase of vancomycin resistance compromises physicians' ability to treat infections caused by many of these strains because often no other antimicrobial drugs are available. Willems, et al., *Emerg. Infect. Dis.*, 11(6):821-8 (2005).

In some embodiments the compositions disclosed herein are used as a topical antibacterial medication for skin infections caused by methicillin-resistant *Staphylococcus aureus*. Methicillin-resistant *Staphylococcus aureus* (MRSA) is a bacteria that is resistant to many antibiotics. The CDC encourages clinicians to consider MRSA in the differential diagnosis of skin and soft tissue infections (SSTIs) compatible with *S. aureus* infections, especially those that are purulent (fluctuant or palpable fluid-filled cavity, yellow or white center, central point or "head," draining pus, or possible to aspirate pus with needle or syringe). A patient's presenting complaint of "spicier bite" should raise suspicion of an *S. aureus* infection. In the community, most MRSA infections are skin infections. In other embodiments, the compositions can be used to treat systemic infections of lungs or blood caused by methicillin-resistant *Staphylococcus aureus* in hospitalized or immunocompromised patients. In medical facilities, MRSA causes life-threatening bloodstream infections, pneumonia and surgical site infections.

The spectrum of disease caused by MRSA appears to be similar to that of *Staphylococcus aureus* in the community. Soft tissue infections (SSTIs), specifically furuncles (abscessed hair follicles or "boils"), carbuncles (coalesced masses of furuncles), and abscesses, are the most frequently reported clinical manifestations. The most common manifestations of community associated-MRSA are simple skin infections, such as impetigo, boils, abscesses, folliculitis, and cellulitis. Rarer, but more serious manifestations can occur, such as necrotizing fasciitis and pyomyositis (most commonly found in the tropics), necrotizing pneumonia, infective endocarditis (which affects the valves of the heart), and bone and joint infections. Additional conditions include severe or extensive disease (e.g., involving multiple sites of infection) or rapid progression in presence of associated cellulitis, signs and symptoms of systemic illness, associated comorbidities or immunosuppression, extremes of age, abscess in an area difficult to drain (e.g., face, hand, and genitalia), associated septic phlebitis, and lack of response to incision and drainage alone, purulent cellulitis, hospitalized patients with complicated SSTI (cSSTI; defined as patients with deeper soft-tissue infections, surgical/traumatic wound infection, and infected ulcers and burns), osteomyelitis, device-related osteoarticular infections, children with minor skin infections (such as impetigo) and secondarily infected skin lesions (such as eczema, ulcers, or lacerations). The compositions disclosed herein can also be used to treat MRSA infections of the CNS, which include, but are not limited to Meningitis, Brain abscess, subdural empyema, spinal epidural abscess. Reviewed in Liu, et al., *Clin Infect Dis.*, 52(3):e18-55 (2011).

The compositions disclosed herein can also be used to treat infections cause by strains of *Escherichia coli* (drug resistant or otherwise) in subjects especially in immunocompromised patients, *Escherichia coli* is one of the most frequent causes of many common bacterial infections, including cholecystitis, bacteremia, cholangitis, urinary tract infections other clinical infections such as neonatal meningitis and pneumonia. For example, the compositions can be used treat conditions caused by community- and/or hospital-acquired urinary tract infections (UTI's) caused by strains of *Escherichia coli* (drug resistant or otherwise) in immunocompromised patients:

3. Methods of Treating Cancer

The disclosed compounds and derivatives thereof earn be used to inhibit DHFR expressed in cancer cells. Inhibiting DHFR, in cancer cells inhibit the growth and reproduction of the cancer cells and thereby inhibits the growth of the cancer or tumor. Thus, one embodiment provides a method of inhibiting tumor growth in a subject in need thereof by administering an effective amount of one or more of the disclosed DHFR binding compounds to inhibit DHFR expressed in cancer or tumor cells.

The types of cancer that can be treated with the provided compositions and methods include, but are not limited to, the following: bladder, brain, breast, cervical, colo-recital, esophageal, kidney, liver, lung, nasopharangeal, pancreatic, prostate, skin, stomach, uterine, ovarian, testicular and the like. Administration is not limited to the treatment of an existing tumor or infectious disease but can also be used to prevent or lower the risk of developing such diseases in an individual, i.e., for prophylactic use. Potential candidates for prophylactic treatment include individuals with a high risk of developing cancer, i.e., with a personal or familial history of certain types of cancer.

Malignant tumors which may be treated are classified herein according to the embryonic origin of the tissue from which the tumor is derived. Carcinomas are tumors arising from endodermal or ectodermal tissues such as skin or the epithelial lining of internal organs and glands. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

B. Combination Therapies

The disclosed compounds and derivatives thereof can be administered with a second therapeutic, including but not limited to one or more anti-fungal agents, antibacterial agents, anti-cancer agents, and combinations thereof.

Anti-Fungal Agents

A variety of known antifungal agents can be used to prepare the described compositions. A list of potential anti-fungal agents can be found in "Martindale—The Complete Drug Reference", 32nd Ed., Kathleen Parfitt, (1999) on pages 367-389. Suitable antifungals include, without limitation, amphotericin, amorolfine, bifonazole, bromochlorosalicyanilide, buclosamide, butenafine, butoconazole, candicidin, chlordantoin, chiormidazole, chlorphenesin, chlorxylenol, ciclopirox olamine, cilofungin, clotrimazole, croconazole, eberconazole, econazole, enilconazole, fenticlor, fenticonazole, fluconazole, flucytosine, griseofulvin, hachimycin, haloprogin, hydroxystilbamine, isethionate, iodochlorohydroxyquinone, isoconazole, itraconazole, ketoconazole, lanoconazole, luflucarban, mepartricin, miconazole, naftifine, natamycin, neticonazole, nifuroxime, nystatin, omoconazole, oxiconazole, pentamycin, propionic acid, protiofate, pyrrolnitrin, ravuconazole, saperconazole, selenium sulfide, sertaconazole; sulbentine, sulconazole, terbinafine, terconazole, tioconazole, tolciclate, tolnaftate, triacetin, timidazole, undecenoic acid, voriconazole and combinations thereof. Some of these agents are known to have antibacterial activity as well.

In one embodiment, the anti-fungal agent(s) is an azole. Suitable imidazole and triazole antifungal agents are fluconazole, timidazole, secnidazole, miconazole nitrate, econazole, haloprogin, metronidazole, itraconazole, terconazole, posaconazole, ravuconazole, ketoconazole, clotrimazole, sapirconazole and combinations thereof.

In an alternative embodiment, the anti-fungal agent(s) is chlorxylenol, undecyclenic acid, selenium sulfide, iodochlorohydroxyquinone, bromochlorosalicyanilide, triacetin or combinations thereof.

Other antifungal agents include bensuldazic acid, benzoic acid, biphenamine, cloconazole, cloxyquin, dermostatin, halethazole, monensin, oxiconazole, nitrate, pecilocin, pyrithione, rubijervine, terbinafine, ticonazole, and undecylinic acid.

Antibacterial Agents

A variety of known antibacterial agents can be used to prepare the described compositions. A list of potential antibacterial agents can be found in "Martindale—The Complete Drug Reference", 32nd Ed., Kathleen Parfitt, (1999) on pages 112-270. Classes of useful antibacterials include aminoglycosides, antimycobacterials, cephalosporins and beta-lactams, chloramphenicols, glycopeptides, lincosamides, macrolides, penicillins, quinolones, sulphonamides and diaminopyridines, tetracyclines, and miscellaneous. In a preferred embodiment, the antibacterial agent is selected from the group consisting of metronidazole, timidazole, secnidazole, erythromycin, bactoban, mupirocin, neomycin, bacitracin, cicloprox, fluoriquinolones, ofloxacin, cephalexin, dicloxacillin, minocycline, rifampin, famciclovir, clindamycin, tetracycline and gentamycin.

Suitable aminoglycosides include antibiotics derived from Streptomyces and other actinomycetales, including streptomycin, framycetin, kanamycin, neomycin, paromomycin, and tobramycin, as well as gentamycin, sissomycin, netilmycin, isepamicin, and micronomycin.

Suitable antimycobacterials include rifamycin, rifaximin, rifampicin, rifabutinisoniazid, pyrazinamide, ethambutol, streptomycin, thiacetazone, aminosalicylic acid, capreomycin, cycloserine, dapsone, clofazimine, ethionamide, prothionamide, ofloxacin, and minocycline.

Cephalosporins and beta-lactams generally have activity against gram-positive bacteria and newer generations of compounds have activity against gram-negative bacteria as well. Suitable cephalosporins and beta-lactams include:

First generation; cephalothin, cephazolin, cephradine, cephaloridine, cefroxadine, cephadroxil, cefatrizine, cephalexin, pivcephalexin, cefaclor, and cefprozil.

Second generation; cephamandole, cefuroxime axetil, cefonicid, ceforanide, cefotiam, and cephamycin.

Third generation; cefotaxime, cefmenoxime, cefodizime, ceftizoxime, ceftriaxone, cefixime, cefdinir, cefetamet, cefpodoxime, ceftibuten, latamoxef, ceftazidime, cefoperazone, cefpiramide, and cefsulodin.

Fourth generation: cefepime and cefpirome

Other cephalosporins include cefoxitim, cefmetazole, cefotetan, cefbuperazone, cefminox, imipenem, meropenem, aztreonam, carumonam, and loracarbef.

Chloramphenicols inhibit gram positive and gram negative bacteria. Suitable cloramphenicols include chloramphenicol, its sodium succinate derivative, thiamphenicol, and azidamfenicol.

Suitable glycopeptides include vancomycin, teicoplanin, and ramoplanin. Suitable lincosamides include lincomycin and clindamycin, which are used to treat primarily aerobic infections.

Macrolides have a lactam ring to which sugars, are attached. Suitable macrolides include erytjhromycin, as well as spiromycin, oleandomycin, josamycin, kitamycin, midecamycin, rokitamycin, azithromycin, clarithromycin, dirithromycin, roxithromycin, flurithromycin, tylosin; and streptgramins (or synergistins) including pristinamycin, and virginiamycin; and combinations thereof.

Suitable penicillins include natural penicillin and the semisynthetic penicillins F, G, X, K, and V. Newer penicillins include phenethicillin, propicillin, methicilin, cloxacillin, dicloxacillin, flucloxacillin, oxacillin, nafcillin, ampicillin, amoxicillin, bacampicillin, hetacillin, metampicillin, pivampicillin, carbenecillin, carfecillin, carindacillin, sulbenecillin, ticarcillin, azlocillin, mezlocillin, piperacillin, temocillin, mecillinam, and pivemecillinam. Lactamase inhibitors such as clavulanic acid, sulbactam, and tazobacytam are often co-administered.

Suitable quinolones include nalidixic acid, oxolinic acid, cinoxacin, acrosoxacin, pipemedic acid, and the fluoroquinolones flumequine, ciprofloxacin, enoxacin, fleroxacin, grepafloxacin, levofloxacin, lomefloxacin, nadifloxacin, norfloxacin, ofloxacin, pefloxacin, rufloxacin, sparfloxacin, trovafloxacin, danofloxacin, enrofloxacin, and marbofloxacin.

Sulphonamides and diaminopyridines include the original of the "sulfa" drugs, sulphanilamide, and a large number of derivatives, including sulfapyridine, sulfadiazine, sulfafurazole, sulfamethoxazole, sulfadimethoxine, sulfadimethoxydiazine, sulfadoxine, sulfametopyrazine, silver sulfadiazine, mafenide acetate, and sulfasalizine, as well as related compounds including trimethoprim, baquiloprim, brodimoprim, ormetoprim, tetroxoprim, and in combinations with other drugs such as co-trimoxazole.

Tetracyclines are typically broad-spectrum and include the natural products chlortetracycline, oxytetracycline, tetracycline, demeclocycline, and semisynthetic methacycline, doxycycline, and minocycline.

Suitable antibacterial agents that do not fit into one of the categories above include spectinomycin, mupirocin, newmycin, fosfomycin, fusidic acid, polymixins, colistin, bacitracin, gramicidin, tyrothricin, clioquinol, chloroquinaldol, haloquinal, nitrofurantonin, nitroimidazoles (including metronizole, timidazole and secnidazole), and hexamine.

The antibiotic and antifungal agents may be present as the free acid or free base, a pharmaceutically acceptable salt, or as a labile conjugate with an ester or other readily hydrolysable group, which are suitable for complexing with the ion-exchange resin to produce the resinate.

Anti-Cancer Agents

Additional therapeutic agents include conventional cancer therapeutics such as chemotherapeutic agents, cytokines, chemokines, and radiation therapy. The majority of chemotherapeutic drugs can be divided in to: alkylating agents, antimetabolites, anthracyclines, plant alkaloids, topoisomerase inhibitors, and other antitumour agents. All of these drugs affect cell division or DNA synthesis and function in some way. Additional therapeutics include monoclonal antibodies and the new tyrosine kinase inhibitors e.g. imatinib mesylate (GLEEVEC® or GLIVEC®), which directly targets a molecular abnormality in certain types of cancer (chronic myelogenous leukemia, gastrointestinal stromal tumors).

Representative chemotherapeutic agents include, but are not limited to cisplatin, carboplatin, oxaliplatin, mechlorethamine, cyclophosphamide, chlorambucil; vincristine, vinblastine, vinorelbine, vindesine, taxol and derivatives thereof, irinotecan, topotecan, amsacrine, etoposide, etoposide phosphate, teniposide, epipodophyllotoxins, trastuzuinab (HERCEPTIN®), cetuximab, and rituximab (RITUXAN® or MABTHERA®), bevacizumab (AVASTIN®), and combinations thereof.

C. Use as a Sterilizing Agent

The compounds disclosed herein can be used as sterilizing agents, for example in high risk environments such as in hardware from hospitals or healthcare facilities. The World Health Organization (WHO) estimates that at any time, more than 1.4 million people worldwide are affected by infections acquired in hospitals. Cleaning, disinfection and sterilization saves lives and improves patient outcomes. Between 5% and 10% of patients admitted to modern hospitals in the developed world acquire one or more healthcare-associated infections. The Centers for Disease Control and Prevention (CDC) estimate that approximately 1.7 million healthcare-associated infections occur annually in hospitals in the United States, and are associated with nearly 100,000 deaths each year. Healthcare-associated infections are also an important problem in extended care facilities, including nursing homes and rehabilitation units. Transmission of healthcare-associated pathogens most frequently occurs via the hands of healthcare workers, who inadvertently contaminate their hands during various patient care activities. Less frequently, contaminated surfaces in healthcare facilities may contribute to the spread of healthcare-associated pathogens.

The varying levels of disinfection used in a healthcare facility may be defined by Spaulding's Classification (Sehulster, et al., Guidelines for environmental infection control in health-care facilities. Recommendations from CDC and the Healthcare Infection Control Practices Advisory Committee (HICPAC). Chicago Ill.; American Society for Healthcare Engineering/American Hospital Association; 2004). Spaulding's levels, non-critical, semi-critical, and critical, are based on the potential for infectious disease spread via equipment, instruments, and furniture as well as the level of sterility normally required for the body part coming in contact with it. Levels of disinfection that correlate with Spaulding's classification are low, intermediate, high, and sterilization. The US Centers for Disease Control (CDC) has further delineated disinfection levels for environmental surfaces in its "Guidelines for Environmental Infection Control in Health-Care Facilities".

Critical items confer a high risk for infection if they are contaminated with any microorganism. Thus, objects that enter sterile tissue or the vascular system must be sterile because any microbial contamination could transmit disease. This category includes surgical instruments, cardiac and urinary catheters, implants, and ultrasound probes used in sterile body cavities. Semicritical items contact mucous membranes or nonintact skin. This category includes respiratory therapy and anesthesia equipment, some endoscopes, laryngoscope blades, esophageal manometry probes, cystoscopes, anorectal manometry catheters, and diaphragm fitting rings. These medical devices should be free from all microorganisms; however, small numbers of bacterial spores are permissible. Specific examples of critical or semi critical instruments include invasive endoscopes such as laparoscopes, and rigid instruments with no operating channel. Arthroscopes and laparoscopes which are inserted into sterile body cavities as well as accessory instrumentation should be sterile. Other examples include gastroscopes, duodenoscopes, sigmoidoscopes, proctoscopes, colonoscopes, bronchoscopes, and laryngoscopes.

EXAMPLES

Example 1: Binding of NSC309401 to DHFR

Materials and Methods

Binding to DHFR was assessed by thermal shift assay, a method that is independent of the catalytic activity and is dependent on the structural stability of the enzyme, whereby, in the presence of the said compound, the thermal stability of the enzyme increased indicative of binding. The thermal shift assay was performed in a control reaction mix containing 100 mM HEPES pH 7.3, 150 mM NaCl, 5× Syproorange (an extrinsic fluorophore reporter from Invitrogen), 10 micromolar of the protein dihydrofolate reductase in 20 μl reaction mix. The test reaction contained 1 mM of the said compound apart from all the other constituents as mentioned above. Protein melting curves were obtained from samples aliquoted in 96-well plates using a RealPlex quantitative PCR from Eppendorf. The dye was excited at 465 nm and the emission was recorded at 580 nm using the filters employed by the instrument. A heating ramp of 1 degree Celsius/min was used from 25 degree Celsius to 74 degree Celsius and one data point was acquired for each degree increment. Appropriate dye controls and protein controls were incorporated. All the experiments were done with minimum two replicates and the mean value of the replicate Y was considered for further analysis.

Results

An algorithm was used to predict this interaction between the protein dihydrofolate reductase (DHFR) from *Escherichia coli* and the molecule 7-[(4-aminophenyl)methyl]-7H-pyrrolo[3,2-f]quinazoline-1,3-diamine (NSC309401). NSC309401 showed a 30 degree Celsius shift in the midpoint of thermal melting curve leading to the computation of approximately 48 nM dissociation constant that is indicative of tight binding to DHFR.

Further, assays were undertaken and NSC309401 was tested for its effect on growth inhibition of multi-drug resistant *Escherichia coli* (MDREC) (positive control: nitrofurantoin and negative control: DMSO), *Escherichia coli* strain DH5 alpha (positive control: nitrofurantoin and negative control: DMSO), methicillin-resistant *Staphylococcus aureus* (MRSA, ATCC 33591)(Positive control: vancomycin and negative control: DMSO), vancomycin-resistant *Enterococcus faecium* (VREF)(Positive control: chloramphenicol and negative control: DMSO) and antifungal activity against amphotericin-resistant *Candida albicans* (ARCA) (Positive control: 1:1 mixture of amphotericin B/cycloheximide and negative control: DMSO). The NSC309401 displayed MIC-90 values (minimum inhibitory concentration to inhibit 90% growth) that are listed below and are given in Table 1 attached documents.

TABLE 1

The minimum inhibitory concentration for 90% growth inhibition (MIC-90) shown by 7-[(4-aminophenyl) methyl]-7H-pyrrolo [3,2-f] quinazoline-1,3-diamine for various organisms.

| S. No | Organism | MIC (μg/mL) |
|---|---|---|
| 1 | Methicillin-resistant *Staphylococcus aureus* (MRSA) | 031.250 |
| 2 | Multi-drug resistant *Escherichia coil* (MDREC) | 125.000 |
| 3 | *Escherichia coli* DH5α | 007.813 |
| 4 | Amphotericin-resistant *Candida albicans* (ARCA) | 125.000 |
| 5 | Vancomycin-resistant *Enterococcus faecalis* (VREF) | 031.250 |

Example 2: Identification of Candidate Molecules Using FINDSITE$^{comb}$

Materials and Methods

FINDSITE$^{comb}$ was used to improve VLS. An assortment of medically-relevant proteins with differing fold-architectures from diverse organisms including the causative agents of human and primate malaria, *Plasmodium falciparum* and *Plasmodium knowlesi*, an opportunistic pathogen *Escherichia coli*, and proteins implicated in mammalian disorders (from *Homo sapiens* and *Rattus norvegicus*) were tested. For these proteins, top ranked ligands predicted by FINDSITE$^{comb}$ were experimentally assessed for binding by thermal-melt assays. After validating the small molecule binding predictions, their physiological function was tested by their ability to kill bacteria such as multi-drug resistant *E. coli* (MDREC), methicillin-resistant *Staphylococcus aureus* (MRSA), Vancomycin-resistant *Enterococcus faecium* (VREF), and their cytotoxic activity using HCT-116 colon carcinoma tumor cell line.

FIG. 1 shows the flowchart of FINDSITE$^{comb}$ methodology (Zhou, et al., *J. Chem., Info. & Model.,* 53(1):230-240 (2013)) in combination with experimental validation protocol. FINDSITE$^{comb}$ is a composite approach consisting of the improved FINDSITE-based approach (Brylinski, et al., PNAS, 105:129-134 (2008)), FINDSITE$^{filt}$ and the extended FINDSITE-based approach FINDSITE$^X$ (Zhou, et al., *Molecular Pharmaceutics*, 9(6):1775-1784 (2012)). Provided in details below are two FINDSITE-based component approaches and their benchmarking and prediction results.

FINDSITE$^{filt}$ consists mainly of three steps: (A) Finding a sub-set of protein template in the library of holo PDB structures (experimental structures with bound ligands) that are putatively evolutionarily related to the target using target sequence and threading approaches; (B) Filtering the sub-set of holo PDB structures using the target structure (experimental or modeled) and structure comparison methods; (C) Selecting pockets and ligands from the filtered sub-set for binding site and virtual screening predictions.

FINDSITE$^{filt}$ employs a heuristic structure-pocket alignment procedure and a sequence dependent scoring function to rank the holo templates in step (B) above. The alignment is evaluated using the sequence dependent score:

$$SP-\text{score} = \sum_{\text{aligned residue } a,b} BLOSUM62(a, b), \quad (1)$$

where BLOSUM62(a,b) is the BLOSUM62 substitution matrix (Henikoff, et al., *PNAS*, 89:10915-10919 (1992)). Templates are ranked by their SP-scores and the ligands corresponding to the top 100 templates are selected as template ligands for ligand virtual screening.

FINDSITE$^{filt}$'s performance relies on the existence of a sufficient number of holo PDB structures homologous to the target. This is not true for most membrane proteins where even apo structures (structures without bound ligands) are rare. Thus, for some of the most interested drug targets, such as the G-Protein Coupled Receptors (GPCRs) and ion-channels, FINDSITE$^{filt}$ has limited performance. The FINDSITE$^X$ approach was developed to overcome the shortcomings of FINDSITE$^{filt}$ on these kind of targets (Zhou, et al., *Molecular Pharmaceutics*, 9(6):1775-1784 (2012)). FINDSITE$^X$ utilizes experimental binding data without ligand bound experimental structures. To use the benefits from structure comparison, structures of proteins in experimental ligand binding database are modeled. FINDSITE$^X$ Uses the fast version of the structure modeling approach TASSER$^{VMT}$ (Zhou, et al., *Proteins* 80(2):352-361 (2011)) (TASSER$^{VMT}$-lite (Zhou, et al., *Molecular Pharmaceutics* 9(6):1775-1784 (2012)) to create a virtual library of protein-ligand structures analogous to the PDB holo structures but without experimentally solved protein-ligand complex structures. Since there is no reliable pocket information for the virtual halo structure, whole structure comparison of the target to the templates (in the virtual holo structures) using fr-TM-align is used (Pandit, et al., *BMC Bioinformatics*, (9):531 (2008)). To reduce false positives, especially for targets like GPCRs where almost all structures are similar (TM-score>0.4), a sequence dependent score similar to the SP-score in Eq. (1) over the fr-TM-aligned residues is used instead of the TM-score. The ligands of the top first ranked template are used as template ligands for searching against compound library. To identify template-ligand pairs, the DrugBank drug-target relational database and the ChEMBL bioactivity database are used (Wishart, et al., *Nucl Acid Res*, 34(Database):D668-672 (2006) and Gaulton, et al., *Nucl Acid Res*, 40(D1):D1100-1107 (2012)).

FINDSITE$^{comb}$ is the combination of FINDSITE$^{filt}$ that uses holo PDB structures as templates and FINDSITE$^X$ that utilizes two independent ligand binding databases. For a given target and compound library, if there is no target structure input, TASSER$^{VMT}$-lite models the structure. Then, three independent virtual ligand screening runs are conducted: (a) FINDSITE$^{filt}$ using the holo PDB structure library; (b) FINDSITE$^X$ using the DrugBank virtual holo structure library; and (c) FINDSITE$^X$ using the ChEMBL virtual holo structure library. For each virtual screening library, the following score is used to measure the likelihood of a compound to be a true compound of the target:

$$mTC = \frac{\sum_{l=1}^{N_{lg}} TC(L_l, L_{lib})}{N_{lg}} + (1-w) \max_{l \in \{1, \ldots, N_{lg}\}} (TC(L_l, L_{lib})), \quad (2)$$

where TC stands for the Tanimoto Coefficient (Tanimoto, *IBM Interanl Report* 1958 (November 1958), $N_{lg}$ is the number of template ligands from the putative evolutionarily related proteins; $L_l$ and $L_{lib}$ stand for the template ligand and the ligand in the compound library, respectively; w is a weight parameter. The first term is the average TC (Brylinski, et al., *PLoS Computational Biology*, 5(6):e1000405 (2009)). The second term is the maximal TC between a given compound and all the template ligands. Here, w=0.1 was empirically chosen to give more weight to the second term so that when the template ligands are true ligands of the target, they will be favored. For a given compound, three independent virtual screenings give three mTC scores and the maximal score is used for the combined ranking.

To experimentally validate FINDSITE$^{comb}$ under non-trivial conditions, i.e., there are no close homologous templates to the target, excluded all templates having sequence identity >30% to given target in the PDB holo structures, DrugBank targets and ChEMBL targets were excluded.

Example 3: Comparison of FINDSITE$^{comb}$ to Traditional Docking-Based Methods

Materials and Methods

A benchmarking test of FINDSITE$^{comb}$ on the DUD set was previously conducted and compared our results to the state-of-the-art docking-based methods for ligand virtual screening (A Directory of Useful Decoys set (Huang, et al., *J. Med. Chem.*, 49(23):6789-6801 (2006)). The DUD set is designed to help test docking algorithms by providing challenging decoys. It has a total of 2,950 active compounds and a total of 40 protein targets. For each active, there are 36 decoys with similar physical properties (e.g. molecular weight, calculated Log P) but dissimilar topology. Two freely available traditional docking methods AUTODOCK Vina (Trott, et al., *J. Comp, Chem.*, 31:455-461 (2010)) and DOCK 6 (Cross, et al., *J. Chem., Info, Model.*, 49:1455-1474 (2009)) were compared to FINDSITE$^{comb}$. AUTODOCK Vina was tested on the DUD set and shown to be a strong competitor against some commercially distributed docking programs. DOCK 6 is an update of the DOCK 4 program. These two methods represent the state-of-the-art traditional docking-based approaches that are computationally expensive, but do not require a known set of binders for a given target as opposing to traditional ligand similarity-base approaches, FINDSITE$^{comb}$ also does not require a known set of binders for the target, but is an order of magnitude faster than docking methods. Most importantly, FINDSITE$^{comb}$ does not require a high-resolution experimental structure of the target. Thus, it is applicable for screening both large compound library and for genomic scale targets.

The performance of a given approach for virtual screening is evaluated by the Enrichment Factor (EF) within the top x fraction (or 100x %) of the screened library compounds defined as:

$$EF_x = \frac{\text{Number of true positives within top } 100x \text{ \%}}{\text{Total number of true positives} \times x} \quad (3)$$

A true positive is defined as an experimentally known binding ligand/drug or one that has a TC-1 to an experimentally validated binding ligand/drug. For x=0.01, $EF_{0.01}$ ranges from 0 to 100 (100 means that all true positives are within the top 1% of the compound library). Another evaluation quantity employed here is the AUAC (area under accumulative curve of the fraction of true positives versus the fraction of the screened library).

Results

The performance of the three approaches on the DUD set using experimental target structures is shown in Table 2.

TABLE 2

Comparison of methods for the 30 protein DUD set using experimental and modeled structures

| Method | Ave. $EF_{0.01}$ (expt. structure) | Ave. $EF_{0.01}$[a] (modeled structure) | Ave. $EF_{0.1}$ (expt. Structure) | Ave. $EF_{0.1}$ (modeled structure) |
|---|---|---|---|---|
| FINDSITE$^{comb}$ | 14.1 | 13.3 | 4.54 | 4.53 |
| AUTODOCK Vina | 5.45 | 2.39 | 2.48 | 1.40 |
| DOCK 6 | 3.82 | 3.05 | 1.29 | 0.87 |

FINDSITE$^{comb}$ shows about 3 times the $EF_{0.01}$ of AUTODOCK Vina or DOCK 6 for the top 1% selected compounds, with an $EF_{0.01}$ of 13.4 versus 4.80 and 3.72, respectively. FINDSITE$^{comb}$ has significantly better overall performance in terms of its AUAC (0.774 vs. 0.586 and 0.426). Although these studies did not have direct access to some of the commercially available approaches compared in Cross, et al., *J Chem Inf Model*, 49:1455-1474 (2009)), of note, FINDSITE$^{comb}$ has a better AUAC than the best performing GLIDE (v4.5) (Friesner, et. al., *J Med Chem*, 47:1739-1749 (2004) and Halgren, et al., *J Med Chem*, 47:1750-1759 (2004)) (mean AUAC=0.72) and all other compared methods: DOCK 6 (mean AUAC=0.55), FlexX (mean AUAC=0.61) (Kramer, et al., *Proteins*, 37:228-241 (1999)), ICM (mean AUAC=0.63) (Abagyan, et al., *J Comput Chem*, 15:488-506 (1994) and Totrov, et al., *Proteins*, Suppl.: 215-220 (1998)), PhDOCK (mean AUAC-0.59) (Joseph-McCarthy, et al., *Proteins*, 51:172-188 (2003), and Joseph-McCarthy, et al., *Drug Disco Very Ser*, 1:327-347 (2005)) and Surflex (Jain, *J Med Chem*, 46:499-511 (2003), Pham, et al., *J Med Chem*, 49:5856-5868 (2006)); and Jain, *J Comput-Aided Mol Des*, 21:281-306 (2007)) (mean AUAC=0.66) (Cross, et al., *J Chem Inf Model*, 49:1455-1474 (2009)).

Next, the effect of target structure quality on the performance of methods was examined. Table 2 shows the enrichment factors $EF_{0.01}$ and $EF_{0.1}$ of different methods using experimental and modeled target structures for a subset of 30 targets from DUD set.

The other 10 targets are not included because the modeled structures have extended long tails (not compact) and their dimensions are too large for docking methods. The results of FINDSITE$^{comb}$ change very little when modeled structures are used as compared to experimental structures are used. This is not the case for either DOCK6 or AUTODOCK whose performance significantly deteriorates.

Example 4: Large Scale Testing of FINDSITE$^{comb}$ on Generic Drug Targets

Materials and Methods

Since FINDSITE$^{comb}$ is much faster than traditional docking approaches and can use modeled as well as experimental structures, large-scale testing on drug targets (some of which lack experimental structures) can be performed using this method. This kind of test is not feasible for traditional docking methods. FINDSITE$^{comb}$ was tested on a set of 3,576 DrugBank targets that can be modeled using TASSER$^{VMT}$-lite (Wishart, et al., *Nucl Acid Res*, 34(Database):D668-672(2006) and Zhou, et al. *Molecular Pharmaceutics*, 9(6):1775-1784 (2012)). Modeled target structures were used even for those targets that have experimental PDB structures. Drugs of all the 3,576 targets are buried in a background of representative compounds that are culled to TC<0.7 to each other from the ZINC8 library (Irwin, et al., *J Chem Inf Model*, 45:177-182 (2005)). The total number of screened compounds for each target was 74,378 (6,507 drugs+67,871 ZINC8 compounds).

Results

The test results are shown in Table 3.

TABLE 3

Performance of FINDSITE methods for 3,576 drug targets

| Method (binding database) | Average $EF_{0.01}$ | # (%) of targets having $EF_{0.01} > 1$ |
|---|---|---|
| FINDSITE (PDB) | 31.7 | 1526 (43%) |
| FINDSITE$^X$ (DrugBank) | 36.6 | 1714 (48%) |
| FINDSITE$^X$ (ChEMBL) | 9.5 | 566 (16%) |
| FINDSITE$^{filt}$ (PDB) | 46.0 | 2080 (58%) |
| FINDSITE$^{comb}$ | 52.1 | 2333 (65%) |

FINDSITE$^{comb}$ achieves an average enrichment factor of 52 for the top 1% of (viz. ranked within the top 744) selected compounds; moreover, about 65% of the targets have an $EF_{0.01} > 1$ (EF=1.0 is by random selection). Thus, on average about half of the true drugs of typical target will show up within top 1% of the screened compounds. FINDSITE$^{comb}$ will be helpful in enriching true binders for 65% of the targets in a typical genome sequence. Of note, FINDSITE$^{comb}$ is better than any of its individual components. The major contribution to FINDSITE$^{comb}$ is from FINDSITE$^{filt}$ or holo PDB structure templates.

Example 5: Experimental Validation of FINDSITE$^{comb}$

Materials and Methods

For the experimental blind validation of this work, a compound library with molecules from the National Cancer Institute (NCI) and ZINC8 (TC<0.7) as background was used. The open chemical repository maintained by the Developmental Therapeutics Program (DTP) at NCI/NIH is a comprehensive set of small molecules consisting of compounds from the diversity set, mechanistic set, natural product set and approved oncology drug set. Compounds constituting the diversity set were derived from a parent library ~140,000 compounds based on the following criteria: (1) Distinctness of the molecules its pharmacophores and its conformational isomers, (2) Rigidity (5 or fewer rotatable bonds), (3) Planarity and (4) Pharmacologically desirable features. Compounds constituting the mechanistic set were selected from a seed library of 37,836 compounds tested on the NCI human tumor 60 cell line screens and represent compounds that show a broad range of growth inhibition. Compounds in the natural product set were selected from 140,000 compounds in the DTP open repository collection based on (a) origin, (b) purity, (c) structural diversity (differential scaffolds structures with varied functional groups), and (d) availability. The compounds in the approved oncology drug set consist of current FDA-approved drugs.

NCI molecules are easy to obtain. The NCI molecules downloaded from NCI included 1597 molecules from the Diversity Set III, 97 from the Approved Oncology Drugs Set IV, and 118 from the Natural Product Set II (total 1812 NCI molecules). The important fact is that no a priori target-compound binding information was used in both virtual screening and experimental validation. Together with the ZINC8 background, a total of 69683 molecules were screened by FINDSITE$^{comb}$. NCI molecules ranked within the top 1% (i.e. higher than ~700$^{th}$) for each target are subsequently considered for thermal shift experimental validation.

Acquisition and Quantification of Thermal Shift Assays

High throughput thermal shift assays were carried out following established guidelines (Crowther, et al., *Analytical Biochemistry*, 399(2):268-275 (2010) and Niesen, et al., *Nature Protocols*, 2(9):2212-2221 (2007)). Protein melting curves were obtained from samples aliquoted in 96-well plates using a RealPlex quantitative PCR instrument from Eppendorf (Eppendorf, N.Y., USA), with Sypro orange dye from Invitrogen as the fluorescent probe. A uniform final concentration of 5× (supplied as a 5000× stock solution) was used in all experiments. The dye was excited at 465 nm and emission recorded at 580 nm using the instrument's filters. A heating ramp of 1° C./min from 25° C. to 74° C. was used, and one data point acquired for each degree increment. For standardization, different buffers and pH were checked. Thereafter, 100 mM HEPES pH 7.3 and 150 mM NaCl were used in all unfolding experiments. The volume of each reaction was 20 μl, and appropriate dye and protein controls were included. All experiments were done with a minimum of two replicates, with the mean value considered for further analysis. Several drugs/small molecules interact with. Sypro orange and lead to aberrant signal enhancements. An additional control to rule out drug-dye interaction was carried out with all the constituents kept constant except for the protein of interest. The protein/protein-drug curves were reported after subtracting the respective dye alone/drug-dye curves.

Each melting curve was assigned a quality score (Q), the ratio of the melting-associated increase in fluorescence ($\Delta F_{melt}$) to the total fluorescence range ($\Delta F_{total}$). Q=1 is a high-quality curve, while Q=0 indicates no thermal transition (Crowthe, et al., *Analytical Biochemistry*, 399(2):268-275 (2010)). Though an arbitrary Q value cutoff was not applied to judge curve quality, the curves were manually curated with Q values reported. A substantial fraction of ligands tested against the various proteins displayed no thermal transitions, Q=0, or showed multi-step unfolding behavior. These were ignored (see Table 4).

Results

TABLE 4

Results from the thermal shift assays on DHFR, ranked by best ligand binding*.

| Protein | Organism | No. of ligands tested | No. of good curves | No. of +ve$^a$ shifts/% +ve$^a$ shifts | Best hit (NSC) | $\Delta T_m$ (° C.) | $K_D$ (nM)$^b$ | Best hit structure |
|---|---|---|---|---|---|---|---|---|
| DHFR | E. coli | 83 | 32 | 15/46.9 | 309401 | 30.74 | 48.21 | |

DHFR: Dihydrofolate reductase
$^a$Positive thermal shift is indicated by the notation +ve.
$K_D$ indicates dissociation constants.
$^b$The dissociation constant reported in this table are computed from the thermal shifts obtained.
*The values reported in this table are experimental in-vitro values.

Subsequent to standardization, the validity of the top 1% of FINDSITE$^{comb}$'s predictions on the test set of eight diverse proteins was examined. To be conservative, we focused only on those protein/ligand pairs showing single sigmoidal thermal transition curves. The fit to Boltzmann's equation (Eq. 1) was employed to estimate the melting temperature from the observed intensity, I.

$$I = I_{min} + \frac{[I_{max} - I_{min}]}{1 + e^{\left(\frac{Tm-T}{a}\right)}} \quad (4)$$

$I_{min}$ and $I_{max}$ are the minimum and maximum intensities; a denotes the slope of the curve at the transition midpoint temperate, $T_m$ [13]. To estimate thermodynamic parameters, both van't Hoff [79] and Gibbs-Helmholtz analyses were done [80]. To estimate the approximate ligand-binding affinity at $T_m$, equation (2) from reference [81] was used with slight modifications; $\Delta C_p$ is ignored.

$$K_L(T_m) = \frac{\exp\left\{\frac{-\Delta H}{R}\left(\frac{1}{Tm} - \frac{1}{To}\right)\right\}}{[L]} \quad (5)$$

$K_L(T_m)$ is the ligand association constant and [L] is the free ligand concentration at $T_m([L_{Tm}]\sim[L]total$, when $[L]_{total}\gg$the total concentration of protein. $K_D$ is the inverse of $K_L(T_m)$.

To eliminate the possibility of thermal shifts arising because organic molecules form colloidal aggregates (Lo, et al., *Analytical Biochemistry*, 332(1):153-159 (2004)), the complete NCI set was compared to the database of known aggregators. Since the thermal shift assay is incompatible with the presence of detergents, (the method of choice to eliminate aggregation-based thermal shifts), we limited ourselves to estimate chemical similarity to known aggregators. At a stringent TC cutoff of 0.9, none of the molecules reported as possessing either binding or antimicrobial/cytotoxic activities are similar to known aggregators.

Example 6: Antimicrobial and Cytotoxic Assays

Materials and Methods

Antimicrobial and anti-cancer tests were performed as in (Teasdale, et al., *The Journal of Organic Chemistry*, 77(18): 8000-8006 (2012). DHFR binders were tested on *E. coli* DH5α [positive control: Nitrofurantion (10 mg/ml in DMSO, negative control: DMSO], multi-drug resistant *E. coli* SMS-3-4 (ATCC BAA-1743) (MDREC) [positive control: Nitrofurantion (10 mg/ml in DMSO), negative control: DMSO], methicillin-resistant *S. aureus* (ATCC 33591) (MRSA) [positive control: Vancomycin (10 mg/ml in DMSO), negative control: DMSO], vancomycin-resistant *E. faecium* (ATCC700221) (VREF) [positive control: Chloramphenicol (10 mg/ml in DMSO), negative control: DMSO], and colon carcinoma cells HCT-116 [positive control: etoposide (20 μg/ml in DMSO), negative control: DMSO]. Phosphatase (1000001 and 1000006) binders and tryptophanyl tRNA synthetase binders were tested on the colon carcinoma cell line HCT-116.

Results

The results from FINDSITE$^{comb}$'s VLS predictions on eight different proteins and their validation by the thermal shift assay methodology are provided. Prior to assessing the VLS results on the eight protein test set, the thermal shift methodology was validated on three proteins having known binding and nonbinding ligands. Only cognate protein-ligand pairs showed shifts in the transition mid-point of thermal melt curves, $T_m$, while non-cognate ligands displayed no such shifts (FIG. 2).

The methodology was next applied in benchmark mode to eight diverse proteins, viz., FINDSITE$^{comb}$ only considered template proteins whose sequence identities to the target was <30%. Typically on the order of 50 ligands per protein gave interpretable thermal shift curves. Of these, the experiments identified a total of 47 small-molecule/protein binding interactions with μM or better affinities. Ten ligands with apparent nM binding affinities (less than 1 μM) were identified for dihydrofolate reductase from *E. coli* and the two mammalian protein tyrosine phosphatases (PTPs). Except for a small fraction of known inhibitors, which further validated the methodology, most are novel. The prediction percentage success rate ranged from 3.9% of ligands tested for the *P. falciparum* ubiquitin-conjugating enzyme to almost 47% for dihydrofolate reductase from E call (Table 4). This is a major advancement over previously reported success rates (Zolli-Juran, et al., *Bioorganic & Med. Chem. Lett.*, 13(15):2493-2496 (2003)). The small-molecules that displayed biological activity had low μM or nM affinities in the in vitro thermal shift assay (Data not shown). This supports the supposition that their in vivo biological activity might result from binding of the small-molecule with the intended target protein. A more detailed summary of the results is presented below.

*E. coli* Dihydrofolate Reductase (DHFR):

In silica screening of *E. coli* DHFR was carried out with FINDSITE$^{comb}$ in benchmarking mode. The top 1% of predictions, with 83 small-molecules, was assessed for binding. Fifteen ligands, representing 47% of interpretable curves, showed binding. The data is shown in Table 5.

TABLE 5

Summary of virtual ligand screening, thermal shift assay, binding parameters and antibacterial, antifungal and anticancer properties of the hits obtained on *E. coli*. DHFR.

| Identity (NSC) | Rank[a] | TC[b] | Q# | $\Delta T_m$ | $K_D$ (nM)[c] (Approx) | DH5α (MIC) | MDREC (MIC) | MRSA (MIC) | VREF (MIC) | ARCA (MIC) | HCT-116 (IC-50) |
|---|---|---|---|---|---|---|---|---|---|---|---|
| 309401 | 253/52 | 0.675753 | 0.5 | 30.74 | 48.21 | 7.813 | 125 | 31.25 | 31.25 | 125 | 0.130 |
| 740* | 2/1 | 0.934113 | 0.5 | 29.77 | 62.25 | ND | ND | ND | 500 | 500 | 0.048 |
| 339578* | 317/58 | 0.669547 | 1.4 | 27.57 | 114.61 | 62.5 | 250 | 31.25 | 31.25 | 125 | 6.11 |
| 382035* | 46/13 | 0.731313 | 0.5 | 24.58 | 266.13 | ND | ND | 31.25 | 31.25 | 250 | 0.182 |
| 754230* | 27/10 | 0.752937 | 0.1 | 22.38 | 499.42 | ND | ND | ND | ND | ND | <<0.031 |
| 698037* | 3/2 | 0.930956 | 1.3 | 21.88 | 576.90 | ND | ND | ND | 500 | 500 | ND |
| 80735 | 658/98 | 0.648163 | 0.3 | 18.16 | 1710.28 | ND | ND | ND | ND | ND | 10.9 |
| 61642* | 197/41 | 0.683773 | 0.6 | 17.58 | 2030.55 | ND | ND | ND | ND | 250 | ND |
| 123458 | 644/97 | 0.648675 | 0.6 | 14.17 | 5639.99 | ND | ND | ND | ND | ND | ND |
| 159686 | 684/103 | 0.646950 | 0.6 | 11.52 | 12662.83 | ND | ND | ND | ND | ND | ND |
| 157522 | 351/64 | 0.666258 | 0.4 | 10.13 | 19457.54 | ND | ND | ND | ND | ND | ND |
| 379536 | 628/95 | 0.649246 | 0.3 | 8.86 | 28903.82 | ND | ND | ND | ND | ND | ND |
| 55152 | 661/99 | 0.648082 | 0.2 | 5.89 | 73833.22 | ND | ND | ND | ND | ND | ND |
| 130801 | 181/38 | 0.686146 | 1.1 | 5.84 | 75019.46 | ND | ND | ND | ND | ND | ND |
| 50690 | 547/86 | 0.653097 | 0.3 | 0.23 | 463384.94 | ND | ND | ND | ND | ND | ND |

*Indicates reported inhibitors of DHFR independently picked up by our predictions and validated experimentally.
[a]The rank is indicated as total rank across the 69,683 compounds including ZINC background/rank, specified only for the NCI set of 1812 compounds.
[b]Tanimoto coefficient, #, quality score (Q) is the ratio of melting-associated increase in fluorescence ($\Delta F_{melt}$) and total range in fluorescence ($\Delta F_{total}$). A Q value of I represents a high-quality curve, while a value of 0 shows an absence of melting as described earlier (Crowther et al., 2010).
[c]The dissociation constants reported are in this table are computed from the thermal shifts obtained.
ND: non determinable/no significant inhibition Of these 15 hits, representing μM or better binders, six were previously reported inhibitors of DHFRs from various organisms (Kuyper, et al., *J. Med. Chem.*, 39(4):892-903 (1996); Richardson, et al., *J. Med. Chem*, 47(16):4105-4018 (2004); Molina, *IDrugs: Invest. Drugs J.*, 11(7):508-521 (2008); Chen, et al., *Lung Cancer*, 74(1):132-138 (2011); and Chio, et al., *Antimicrobial Agents and Chemotherapy*, 37(9):1914-4923 (1993)). Among these known binding molecules, methotrexate (NSC740) showed the maximum thermal shift of ~30° C. followed by 7H-Pyrrolo(3,2-f) quinazoline-1,3-diamine (NSC339578) (Kuyper, et al., *J. Med. Chem.*, 39(4):892903 (1996)), methylbezoprim (NSC382035) (Richardson, et al., *J. Med Chem.*, 47(16): 4105-4018 (2004)), pralatrexate (NSC754230) (Molina, *IDrugs: Invest. Drugs* 1, 11(7):508-521 (2008)), pemetrexed (NSC698037) (Chen, et al., *Lung Cancer*, 74(1):132-138 (2011)) and 6,7-bis(4-aminophenyl) pteridine-2,4-diamine (NSC61642) (Chio, et al., *Antimicrobial Agents and Chemotherapy*, 37(9):1914-1923 (1993)). The approximate dissociation constant ($K_D$) of 62 nM for the enzyme-methotrexate (NSC740) complex matches reported literature values, which range from 2 to 50 nM, within experimental error. Thus, the thermal shift methodology provides an approximate $K_D$. The five other known inhibitors bind DHFR with low μM or nM $K_D$s.

Figure 3B:
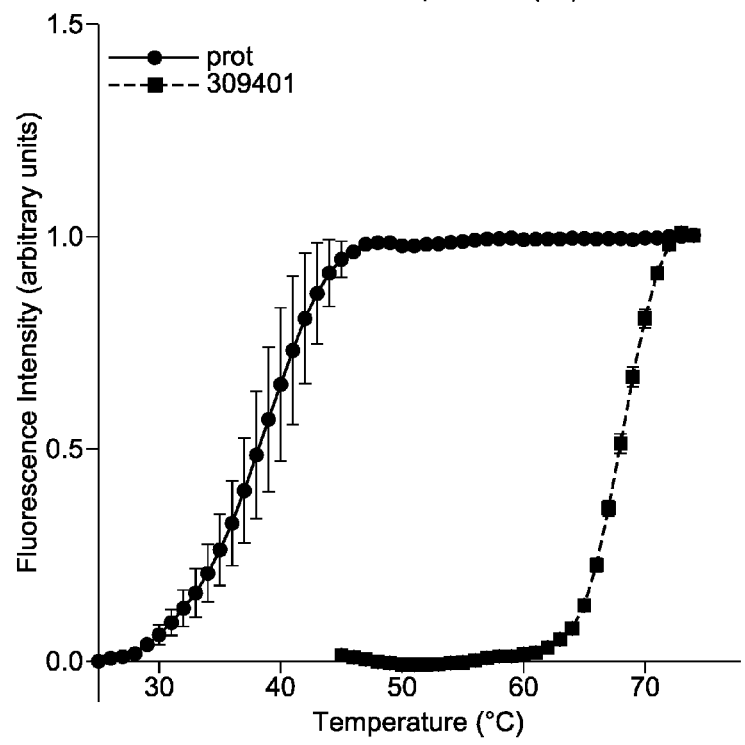
FIG. 3B shows the thermal shift brought about by the binding of the molecule 7-[(4-aminophenyl)methyl]-7H-pyrrolo[3,2-f]quinazoline-1,3-diamamine to the protein dihydrofolate reductase (DHFR) from *E. coli*.

Nine small molecules are novel hits with no reported binding to/activity against DHFRs. These molecules are chemically diverse. The 15 different hits cluster into 10 distinct chemical classes based on a Tanimoto coefficient (TC) cutoff of 0.7. NSC309401, the top novel hit in Table 5, showed apparently better binding to *E. coli* DHFR than methotrexate ($K_D$ of 48 nM and a thermal shift of almost 31 degrees) and showed inhibition against several antibiotic-resistant microbial strains (Table 6) and FIG. 3B.

TABLE 6

Antimicrobial and anticancer activities of a representative set of small-molecules[b].

| Protein[a] | Identity (NSC) | DH5α (MIC) | MDREC (MIC) | MRSA (MIC) | VREF (MIC) | HCT-116 (IC-50) |
|---|---|---|---|---|---|---|
| DHFR | 309401 | 7.813 | 125 | 31.25 | 31.25 | 0.130 |
|  | 740* | ND | ND | ND | 500 | 0.048 |
|  | 339578* | 62.5 | 250 | 31.25 | 31.25 | 6.11 |
|  | 382035* | ND | ND | 31.25 | 31.25 | 0.182 |
|  | 754230* | ND | ND | ND | ND | <<0.031 |

*Reported inhibitors of DHFR independently picked up by the predictions in these studies and validated experimentally,
MIC: Minimum inhibitory concentration required for 90% clearance, μg/mL units.
ND: No significant inhibition.
NA: not applicable.
DH5α: *E. coli* strain DH5α,
MRSA: Methicillin-resistant *S. aureus*,
MDREC; Multi-drug resistant *E. coli*,
VREF: Vancomycin-resistant *E. faecium*,
HCT-116: Colon carcinoma cell line.
IC-50: inhibitory concentration for 50% growth inhibition, μg/mL units.
[b]The values reported in this table are experimental in-vitro values.

NSC309401 displayed a promising MIC of 7.8 μg/mL against *E. coli* DH5α and a reasonable MIC (31.25 μg/mL) against MRSA and VREF. It also has very potent activity against the HCT-116 colon carcinoma cell line with an IC-50 of 0.13 μg/mL (Table 5).

The data corroborate findings from the NCI human tumor cell line growth inhibition assay showing that this molecule has activity (potency not revealed) against several cancer cell lines including melanoma, prostrate, colon, and breast (Wang, et al., *Nucleic Acids Research*, 40(Database issue): D400-412 (2012). Its activity is at least partly due to DHFR inhibition. Since NSC309401 inhibits both prokaryotic and eukaryotic systems, it might be a broad specificity antifolate. 2,4-diaminoquinazolines and their derivatives are known to inhibit DHFR (a prominent example is trimetrexate) but their structures are different from NSC309401, a 7-[(4-aminophenyl)methyl]-7Hpyrrolo[3,2-f]quinazoline-1,3-diamine, in that the latter compound has a novel tricyclic heterocycle.

Another interesting small molecule, with no previously reported binding to DHFR, was NSC80735, with a $K_D$ of 1.7 μM and a MIC of 10.9 μg/mL against HCT-116 (Table 5). The other novel hits had affinities ranging from 6-75 μM; these hits represent potential compounds that could be improved to increase their medical significance vis-à-vis DHFR inhibition. A single novel hit had a poor affinity of ~460 μM.

Modifications and variations of the invention described herein will be obvious to those skilled in the art and are intended to come within the scope of the appended claims

We claim:

1. A method of treating a bacterial or fungal infection in a subject in need thereof by inhibiting dihydrofolate reductase in the microbe, the method comprising administering an effective amount of a compound according to Formula I

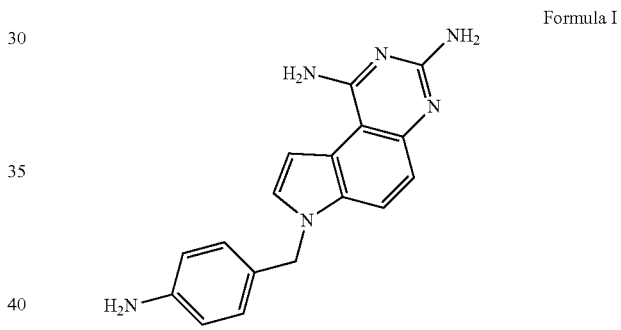

Formula I to the subject to inhibit dihydrofolate reductase in the bacteria or fungi of the infection, wherein the bacteria or fungi are selected from the group consisting of methicillin-resistant *S. aureus* (MRSA), vancomycin-resistant enterococci (VRE), vancomycin-resistant *S. aureus* (VRSA), drug resistant *E. coli*, amphotericin-resistant *Candida albicans* (ARCA) and combinations thereof.

2. The method of claim 1, wherein the compound is administered parenterally or orally.

3. The method of claim 1, wherein the infection is an infection caused by vancomycin-resistant strains of *Enterococcus faecalis* (VREF).

4. The method of claim 1, wherein the infection is caused by methicillin-resistant *S. aureus*.

5. The method of claim 1, wherein the infection is selected from the group consisting of impetigo, boils, abscesses, folliculitis, cellulitis, necrotizing fasciitis, pyomyositis, surgical/traumatic wound infection, and infected ulcers and burns, osteomyelitis, device-related osteoarticular infections, secondarily infected skin lesions, meningitis, brain abscess, subdural empyema, blood infections and spinal epidural abscess.

6. The method of claim 1, wherein the infection is caused by a drug-resistant strain of *E. coli*.

7. The method of claim 6, wherein the infection is a urinary tract infection.

8. The method of claim 1, wherein the subject is hospitalized or immunocompromised.

9. A method of treating a bacterial or fungal infection in a subject in need thereof by inhibiting dihydrofolate reductase in the microbe, the method comprising administering an effective amount of a compound according to Formula I

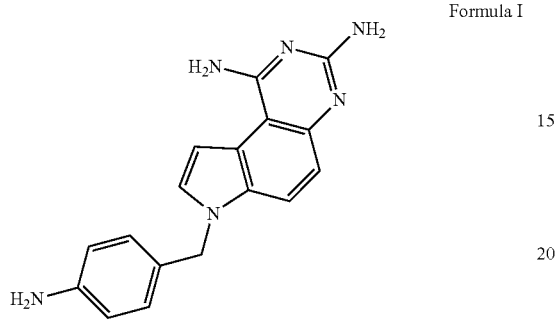

Formula I to the subject to inhibit dihydrofolate reductase in the bacteria or fungi of the infection, wherein the bacteria or fungi are selected from the group consisting vancomycin-resistant enterococci (VRE), vancomycin-resistant *S. aureus* (VRSA), drug resistant *E. coli*, amphotericin-resistant *Candida albicans* (ARCA) and combinations thereof.

* * * * *